United States Patent
Palackal et al.

(10) Patent No.: US 8,440,417 B2
(45) Date of Patent: May 14, 2013

(54) METHOD FOR ASSAYING COMPOUNDS OR AGENTS FOR ABILITY TO DISPLACE POTENT LIGANDS OF HEMATOPOIETIC PROSTAGLANDIN D SYNTHASE

(75) Inventors: Nisha Palackal, Ann Arbor, MI (US); Jeffrey K. Johnson, Ann Arbor, MI (US); Karie L. McGowan, Manchester, MI (US); Kirk W. Maxey, Ann Arbor, MI (US); Gregory W. Endres, Saline, MI (US)

(73) Assignee: Cayman Chemical Company, Incorporated, Ann Arbor, MI (US)

( * ) Notice: Subject to any disclaimer, the term of this patent is extended or adjusted under 35 U.S.C. 154(b) by 694 days.

(21) Appl. No.: 12/465,332

(22) Filed: May 13, 2009

(65) Prior Publication Data

US 2009/0286261 A1    Nov. 19, 2009

Related U.S. Application Data

(60) Provisional application No. 61/052,826, filed on May 13, 2008.

(51) Int. Cl.
| | |
|---|---|
| *G01N 21/00* | (2006.01) |
| *G01N 33/53* | (2006.01) |
| *G01N 33/542* | (2006.01) |

(52) U.S. Cl.
USPC ................ 435/7.6; 435/4; 435/7.4; 435/7.71; 435/7.9; 435/39; 436/8; 436/164; 436/166

(58) Field of Classification Search ........................ None
See application file for complete search history.

(56) References Cited

U.S. PATENT DOCUMENTS

| | | | |
|---|---|---|---|
| 2004/0082021 A1* | 4/2004 | Li et al. | 435/7.92 |
| 2004/0152148 A1 | 8/2004 | Lambalot | |
| 2007/0269841 A1 | 11/2007 | Sprint et al. | |
| 2008/0146569 A1 | 6/2008 | Blake et al. | |
| 2008/0207651 A1 | 8/2008 | Blake et al. | |
| 2008/0227782 A1 | 9/2008 | Aldous et al. | |

FOREIGN PATENT DOCUMENTS

| | | | |
|---|---|---|---|
| AU | 2006267454 A1 | | 7/2006 |
| WO | WO 2004/016223 | * | 2/2004 |
| WO | WO2006015195 A1 | | 2/2006 |
| WO | WO 2007/041634 | * | 4/2007 |

(Continued)

OTHER PUBLICATIONS

Seethala, R., et al., "A Rapid, homogeneous, fluorescence polarization binding assay for peroxisome profilerator-activated receptors alpha and gamma using a fluorescein-tagged dual PPARα/γ activator," Analytical Biochemistry, vol. 363, pp. 263-274, 2007.

(Continued)

*Primary Examiner* — Ja'Na Hines
(74) *Attorney, Agent, or Firm* — Howard & Howard Attorneys PLLC

(57) ABSTRACT

An exemplary embodiment may be directed to a fluorescence polarization assay that screens compounds or agents for their affinity to hematopoietic prostaglandin D synthase (H-PGDS) based on their ability to displace a fluorophore-containing detection analyte bound to an enzyme comprising the primary amino acid sequence of H-PGDS. Another exemplary embodiment utilizes an enzyme having a maltose binding protein amino-acid sequence fused with an N-terminus of the enzyme.

1 Claim, 14 Drawing Sheets

5-Carboxyfluorescein, succinimidyl ester
(5-FAM, SE)

5-Carboxytetramethylrhodamine, succinimidyl ester
(5-TAMRA, SE)

5-Carboxy-X-rhodamine, succinimidyl ester
(5-ROX, SE)

Texas Red sulfonyl chloride
(Sulforhodamine 101 sulfonyl chloride)

FOREIGN PATENT DOCUMENTS

| | | |
|---|---|---|
| WO | WO2007041634 A1 | 4/2007 |
| WO | WO2008075172 A2 | 6/2008 |
| WO | WO2008104869 A1 | 9/2008 |
| WO | WO2008122787 A1 | 10/2008 |

OTHER PUBLICATIONS

Spik, I., Brenuchon, C., Angeli, V., et al. J. Immunol., 2005, 174, 3703-3708.

Urade, Y., Hayaishi, O. Vitamin and Hormones, 2000, 58, 89-120.

Aritake, K., Kado, Y., Inoue, T., Miyano, M. Urade, Y. J. Biol. Chem., 2006, 281, 15277-15286.

Kanaoka, Y., Fujimora, K., Kikuno. R., et a., Eur. J. Biochem., 2000, 267, 3315-3322.

Kanaoka, Y., Ago, H., Inagaki, E., et al., Cell, 1997, 90, 1085-1095.

Urade, Y., Fujimoto, N., Ujihara, M., et al., J. Biol. Chem., 1987, 262(8), 3820-3825.

Matsushita, N., Hizue, M., Aritake, K. Hayashi, K., Takada, A., Mitsui, K., Hayashi, M., Hirotsu, I., Kimura, Y., Tani, T., Nakajima, H. Jpn, J. Pharmacol., 1998, 78, 1-10.

Greig, G.M., Masse, F., Nantel, F., et al., J. Allergy Clin. Immunol, 2006, 117(Suppl. 2) S66.

Burke, T.J., Loniello, K.R., Beebe, J.A., Ervin, K.M., Comb. Chem. High Throughput Screen., 2003, 6(3), 183-194.

Hohwy, M., Spadola, L., Lundquist, B., et al., J. Medicinal Chem., 2008, 51(7), 2178-2186.

Zhang, J.H., Chung, T.D.Y., and Oldenburg, K.R. J. Biomolecular Screenings, 1999, 4(2), 67-73.

Abstract MEDI 26 (poster) Division of Medicinal Chemistry, American Chemical Society National Meeting, New Orleans, LA, Apr. 6-10, 2008; Example 36 (Taiho).

Morten Hohwy et al., Novel Prostaglandin D Synthase Inhibitors Generated by Fragment-Based Drug Design, J. Med. Chem. 2008, 51, 2178-2186, Published on Web Mar. 15, 2008.

* cited by examiner

FIGURE 1
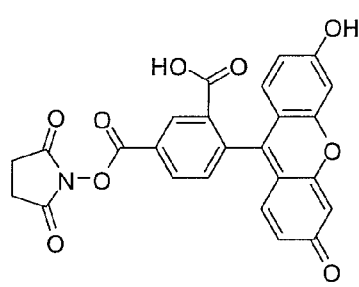
5-Carboxyfluorescein, succinimidyl ester
(5-FAM, SE)
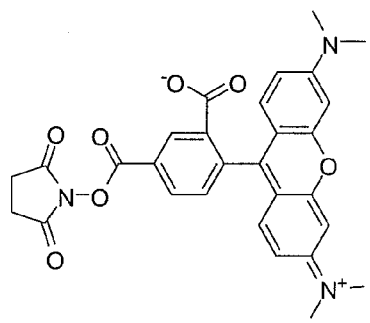
5-Carboxytetramethylrhodamine, succinimidyl ester
(5-TAMRA, SE)
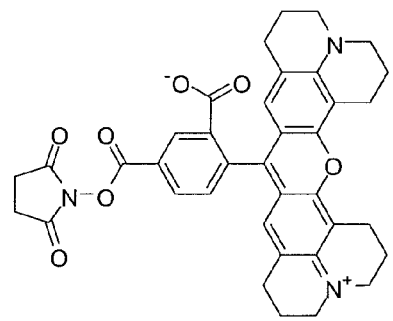
5-Carboxy-X-rhodamine, succinimidyl ester
(5-ROX, SE)
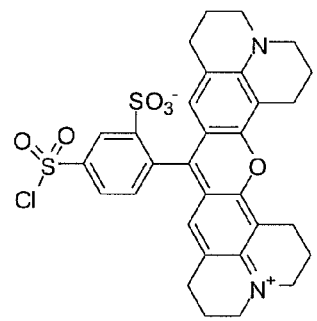
Texas Red sulfonyl chloride
(Sulforhodamine 101 sulfonyl chloride)

FIGURE 3

MHHHHHHPNYKLTYFNMRGRAEIIRYIFAYLDIQYEDHRIEQADWPEIKSTLPFGKIPILE
VDGLTLHQSLAIARYLTKNTDLAGNTEMEQCHVDAIVDTLDDFMSCFPWAEKKQDVKE
QMFNELLTYNAPHLMQDLDTYLGGREWLIGNSVTWADFYWEICSTTLLVFKPDLLDNH
PRLVTLRKKVQAIPAVANWIKRRPQTKL

| 1 | | | | 5 | | | | 10 | | | | 15 | | |
|---|---|---|---|---|---|---|---|---|---|---|---|---|---|---|

Met His His His His His His Pro Asn Tyr Lys Leu Thr Tyr Phe Asn
Met Arg Gly Arg Ala Glu Ile Ile Arg Tyr Ile Phe Ala Tyr Leu Asp
Ile Gln Tyr Glu Asp His Arg Ile Glu Gln Ala Asp Trp Pro Glu Ile
Lys Ser Thr Leu Pro Phe Gly Lys Ile Pro Ile Leu Glu Val Asp Gly
Leu Thr Leu His Gln Ser Leu Ala Ile Ala Arg Tyr Leu Thr Lys Asn
Thr Asp Leu Ala Gly Asn Thr Glu Met Glu Gln Cys His Val Asp Ala
Ile Val Asp Thr Leu Asp Asp Phe Met Ser Cys Phe Pro Trp Ala Glu
Lys Lys Gln Asp Val Lys Glu Gln Met Phe Asn Glu Leu Leu Thr Tyr
Asn Ala Pro His Leu Met Gln Asp Leu Asp Thr Tyr Leu Gly Gly Arg
Glu Trp Leu Ile Gly Asn Ser Val Thr Trp Ala Asp Phe Tyr Trp Glu
Ile Cys Ser Thr Thr Leu Leu Val Phe Lys Pro Asp Leu Leu Asp Asn
His Pro Arg Leu Val Thr Leu Arg Lys Lys Val Gln Ala Ile Pro Ala
Val Ala Asn Trp Ile Lys Arg Arg Pro Gln Thr Lys Leu 1          5          10          15

Based on accession number: NM_014485

FIGURE 6

MKIEEGKLVIWINGDKGYNGLAEVGKKFEKDTGIKVTVEHPDKLEEKFPQVAATGDGP
DIIFWAHDRFGGYAQSGLLAEITPDKAFQDKLYPFTWDAVRYNGKLIAYPIAVEALSLIY
NKDLLPNPPKTWEEIPALDKELKAKGKSALMFNLQEPYFTWPLIAADGGYAFKYENGK
YDIKDVGVDNAGAKAGLTFLVDLIKNKHMNADTDYSIAEAAFNKGETAMTINGPWAWS
NIDTSKVNYGVTVLPTFKGQPSKPFVGVLSAGINAASPNKELAKEFLENYLLTDEGLEA
VNKDKPLGAVALKSYEEELAKDPRIAATMENAQKGEIMPNIPQMSAFWYAVRTAVINAA
SGRQTVDEALKDAQTNSSSNNNNNNNNNNLGIEGRISEFGSPNYKLTYFNMRGRAEII
RYIFAYLDIQYEDHRIEQADWPEIKSTLPFGKIPILEVDGLTLHQSLAIARYLTKNTDLAG
NTEMEQCHVDAIVDTLDDFMSCFPWAEKKQDVKEQMFNELLTYNAPHLMQDLDTYLG
GREWLIGNSVTWADFYWEICSTTLLVFKPDLLDNHPRLVTLRKKVQAIPAVANWIKRRP
QTKL

FIGURE 6 (Cont)

```
        1               5               10              15
Met Lys Ile Glu Glu Gly Lys Leu Val Ile Trp Ile Asn Gly Asp Lys
Gly Tyr Asn Gly Leu Ala Glu Val Gly Lys Lys Phe Glu Lys Asp Thr
Gly Ile Lys Val Thr Val Glu His Pro Asp Lys Leu Glu Glu Lys Phe
Pro Gln Val Ala Ala Thr Gly Asp Gly Pro Asp Ile Ile Phe Trp Ala
His Asp Arg Phe Gly Gly Tyr Ala Gln Ser Gly Leu Leu Ala Glu Ile
Thr Pro Asp Lys Ala Phe Gln Asp Lys Leu Tyr Pro Phe Thr Trp Asp
Ala Val Arg Tyr Asn Gly Lys Leu Ile Ala Tyr Pro Ile Ala Val Glu
Ala Leu Ser Leu Ile Tyr Asn Lys Asp Leu Leu Pro Asn Pro Pro Lys
Thr Trp Glu Glu Ile Pro Ala Leu Asp Lys Glu Leu Lys Ala Lys Gly
Lys Ser Ala Leu Met Phe Asn Leu Gln Glu Pro Tyr Phe Thr Trp Pro
Leu Ile Ala Ala Asp Gly Gly Tyr Ala Phe Lys Tyr Glu Asn Gly Lys
Tyr Asp Ile Lys Asp Val Gly Val Asp Asn Ala Gly Ala Lys Ala Gly
Leu Thr Phe Leu Val Asp Leu Ile Lys Asn Lys His Met Asn Ala Asp
Thr Asp Tyr Ser Ile Ala Glu Ala Ala Phe Asn Lys Gly Glu Thr Ala
Met Thr Ile Asn Gly Pro Trp Ala Trp Ser Asn Ile Asp Thr Ser Lys
Val Asn Tyr Gly Val Thr Val Leu Pro Thr Phe Lys Gly Gln Pro Ser
Lys Pro Phe Val Gly Val Leu Ser Ala Gly Ile Asn Ala Ala Ser Pro
Asn Lys Glu Leu Ala Lys Glu Phe Leu Glu Asn Tyr Leu Leu Thr Asp
Glu Gly Leu Glu Ala Val Asn Lys Asp Lys Pro Leu Gly Ala Val Ala
Leu Lys Ser Tyr Glu Glu Glu Leu Ala Lys Asp Pro Arg Ile Ala Ala
Thr Met Glu Asn Ala Gln Lys Gly Glu Ile Met Pro Asn Ile Pro Gln
Met Ser Ala Phe Trp Tyr Ala Val Arg Thr Ala Val Ile Asn Ala Ala
Ser Gly Arg Gln Thr Val Asp Glu Ala Leu Lys Asp Ala Gln Thr Asn
Ser Ser Ser Asn Asn Asn Asn Asn Asn Asn Asn Asn Asn Leu Gly Ile
Glu Gly Arg Ile Ser Glu Phe Gly Ser Pro Asn Tyr Lys Leu Thr Tyr
Phe Asn Met Arg Gly Arg Ala Glu Ile Ile Arg Tyr Ile Phe Ala Tyr
Leu Asp Ile Gln Tyr Glu Asp His Arg Ile Glu Gln Ala Asp Trp Pro
Glu Ile Lys Ser Thr Leu Pro Phe Gly Lys Ile Pro Ile Leu Glu Val
```

FIGURE 6 (Cont)

```
 1              5              10             15
Asp Gly Leu Thr Leu His Gln Ser Leu Ala Ile Ala Arg Tyr Leu Thr
Lys Asn Thr Asp Leu Ala Gly Asn Thr Glu Met Glu Gln Cys His Val
Asp Ala Ile Val Asp Thr Leu Asp Asp Phe Met Ser Cys Phe Pro Trp
Ala Glu Lys Lys Gln Asp Val Lys Glu Gln Met Phe Asn Glu Leu Leu
Thr Tyr Asn Ala Pro His Leu Met Gln Asp Leu Asp Thr Tyr Leu Gly
Gly Arg Glu Trp Leu Ile Gly Asn Ser Val Thr Trp Ala Asp Phe Tyr
Trp Glu Ile Cys Ser Thr Thr Leu Leu Val Phe Lys Pro Asp Leu Leu
Asp Asn His Pro Arg Leu Val Thr Leu Arg Lys Lys Val Gln Ala Ile
Pro Ala Val Ala Asn Trp Ile Lys Arg Arg Pro Gln Thr Lys Leu
 1              5              10             15
```

Z'-Factor Determination

METHOD FOR ASSAYING COMPOUNDS OR AGENTS FOR ABILITY TO DISPLACE POTENT LIGANDS OF HEMATOPOIETIC PROSTAGLANDIN D SYNTHASE

CROSS REFERENCE TO RELATED APPLICATIONS

The present invention claims priority from U.S. Provisional Application No. 61/052,826, filed on May 13, 2008.

FIELD OF THE INVENTION

The present invention relates to a fluorescence polarization assay for the screening of compounds for their affinity to hematopoietic prostaglandin D synthase (H-PGDS).

BACKGROUND OF THE INVENTION

Prostaglandin $D_2$ ($PGD_2$) is a naturally occurring prostaglandin that has been shown to be a mediator in allergic and inflammatory disorders (Spik, I., Brenuchon, C., Angeli, V., et al. *J. Immunol.*, 2005, 174, 3703-3708; Urade, Y., Hayaishi, O. *Vitamin and Hormones,* 2000, 58, 89-120). $PGD_2$ is formed from arachidonic acid by reactions catalyzed by prostaglandin endoperoxide synthase (cyclooxygenase, COX) and PGD synthase (PGDS). COX catalyzes two consecutive reactions, dioxygenation of arachidonic acid to $PGG_2$ and peroxidation of $PGG_2$ to $PGH_2$, the common precursor of prostanoids (Aritake, K., Kado, Y., Inoue, T., Miyano, M., Urade, Y. *J. Biol. Chem.,* 2006, 281, 15277-15286). $PGH_2$ metabolism leads to $PGE_9$. $PGD_2$, $PGF_2$, $PGI_2$ and thromboxane $A_2$ ($TXA_2$).

Two distinct types of prostaglandin D synthases are involved in $PGD_2$ production: lipocalin-type PGDS (L-PGDS) and hematopoietic PGDS (H-PGDS). L-PGDS and H-PGDS differ with respect to primary amino acid sequence, cellular localization and tertiary structure. L-PGDS, also known as β-trace, is localized in the central nervous system, male genital organs, and heart and is involved in the regulation of sleep and pain (Aritake et al., 2006). H-PGDS is associated with allergic and inflammatory reactions due to its localization in mast cells, Th2 cells, microglia, necrotic muscle fibers and apoptotic smooth muscle cells (Aritake et al., 2006). H-PGDS requires glutathione for activity and belongs to the sigma-class of glutathione S-transferases (Kanaoka, Y., Fujimora, K., Kikuno, R., et al. *Eur. J. Biochem.,* 2000, 267, 3315-3322; Kanaoka, Y., Ago, H., Inagaki, E., et al., *Cell,* 1997, 90, 1085-1095; Urade, Y., Fujimoto, N., Ujihara, M., et al., *J. Biol. Chem.,* 1987, 262(8), 3820-3825). Two well-known H-PGDS inhibitors, namely HQL-79 and Tranilast, have both been shown to reduce $PGD_2$ levels in guinea pig lung tissues chronically treated with the inhibitors (Matsushita, N., Hizue, M., Aritake, K., Hayashi, K., Takada, A., Mitsui, K., Hayashi, M., Hirotsu, I., Kimura, Y., Tani, T., Nakajima, H. *Jpn. J. Pharmacol.,* 1998, 78, 1-10). Both inhibitors possess micromolar $IC_{50}$ values against the synthase in known in vitro assays. Recent patent application publications describe pyrimidine amide compounds (U.S. Appn. No. 2008/0207651 to Blake et al., entitled "Heterocyclic Compounds Useful in Treating Disease and Conditions; U.S. Appn. No. 2008/0227782 to Aldous et al., entitled "Pyrimidine Amide Compounds as PGDS Inhibitors") and pyridine amide compounds (U.S. Appn. No. 2008/0146569 to Blake et al., entitled "Nicotinamide Derivatives") as H-PGDS inhibitors with nanomolar $IC_{50}s$.

Currently known in vitro H-PGDS inhibition assays typically quantify $PGD_2$ production using $PGD_2$ enzyme immunoassays (EIAs), fluorescence polarization enzyme immunoassays (FPIAs), or the corresponding radioimmunoassay (RIAs) in order to determine a compound's or agent's ability to modulate $PGD_2$ production. These functional assays utilize the unstable prostanoid precursor $PGH_2$ as the H-PGDS substrate. $PGH_2$ can non-enzymatically convert to $PGD_2$ and $PGE_2$ and thus assays that measure $PGD_2$ production from $PGH_2$ must employ cumbersome and precisely-timed reaction and quenching sequences in order to minimize non-enzymatic production of $PGD_2$. These assays are not amenable to high-throughput screening (HTS).

Other in vitro H-PGDS assays involve the use of glutathione S-transferase (GST) substrates such as chloro-dinitrobenzene (CDNB) or monochlorobimane (MCB), in which the conjugation of glutathione (GSH) to CDNB or MCB is measured by colorimetry or fluorometry, respectively. (Greig, G. M., Masse, F., Nantel, F., et al., *J. Allergy Clin. Immunol.,* 2006, 117 (Suppl. 2), S66). A limitation of this assay could be that it would select for inhibitors that can also inhibit endogenous GSTs. GSTs are important detoxifying enzymes and are known to play significant role in xenobiotic metabolism and inhibiting these enzymes could have toxicological implications downstream. Another potential limitation inherent in GST assays is the general bias of these assays toward compounds that may conjugate directly with GSH but do not bind to H-PGDS in eukaryotic cells. Finally, the ability of CDNB and MCB to conjugate with GSH non-enzymatically, can cause low signal-to-noise ratios and narrow dynamic range in these assays.

A known cell-based assay that simultaneously measures potency, specificity, and cytotoxicity of H-PGDS modulators involves stimulation of the arachidonic acid cascade in any mammalian cell line in which human $PGD_2$ is expressed as described in WO 2006/015195 to Yang et al., entitled "Method for Determining the Potency, Specificity, and Toxicity of Hematopoietic D2 Synthase."

Fluorescence polarization (FP) assays provide advantages in the study of protein-ligand binding over conventional methods such as those described above. FP assays allow real-time measurements, avoid the use of radioactive materials, are homogeneous, typically comprise fewer steps (require no washing step), and may possess sub-nanomolar detection limits. FP assays are currently used in drug discovery and are routinely converted to high-throughput screening (HTS) format (Burke, T. J., Loniello, K. R., Beebe, J. A., Ervin, K. M. *Comb. Chem. High Throughput Screen.,* 2003, 6(3), 183-194).

Fluorescence is one of a number of phenomena generally referred to as luminescence. Fluorescence is a luminescence in which the molecular absorption of a photon of a specific wavelength (excitation wavelength) triggers the emission of a photon of longer (lower-energy) wavelength, while the remainder of the absorbed energy is usually translated into increased molecular motion or thermal energy. The molecular component of a fluorescent substance that causes it to fluoresce is called the fluorophore. The photon of a particular frequency ($v_{ex}$) promotes a fluorophore from its ground-state ($S_0$) into an excited state ($S_1$):

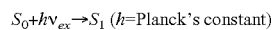

$S_0 + hv_{ex} \rightarrow S_1$ ($h$=Planck's constant)

Fluorescence occurs with the transition of a fluorophore excited-state electron to its ground state, which is accompanied by the emission of a longer-wavelength, lower-frequency photon ($v_{em}$):

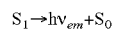

$S_1 \rightarrow hv_{em} + S_0$

Fluorescence polarization operates on the principle that when a fluorescent molecule is excited with polarized light, light is emitted in the same polarized plane if the excitation lifetime is less than the time it takes for the molecule to tumble out of this plane. Should the high-energy state exist longer than the time it takes for the molecule to tumble out of the excitation plane, light is emitted in a plane different from the excitation plane, which results in the detection of a relatively depolarized signal. Very large, high-mass molecules are less likely to rotate out of the excitation plane prior to emission and are therefore more likely to emit highly polarized light and produce a strong polarization signal. Smaller molecules are more likely to tumble out of the excitation plane prior to relaxation and emission and therefore provide relatively depolarized (relative to the excitation plane) emitted light and a weaker FP signal. To evaluate the polarization two measurements are needed: the first using a polarized emission filter parallel to the excitation filter (S-plane) and the second with a polarized emission filter perpendicular to the excitation filter (P-plane). The fluorescence polarization response is given as mP (milli-Polarization) level and is obtained from the equation:

Polarization (mP)=1000×[S−(G×P)]/[(S+(G×P)]

where S and P are background subtracted fluorescence count rates and G (grating) is an instrument and assay dependent factor. The rotational speed of a molecule is dependent on the size of the molecule, temperature and viscosity of the solution. Fluorescein, rhodamine, and DyLight™ 633 have fluorescence lifetimes suitable for the rotation speeds of molecules in bio-affinity assays such as receptor-ligand binding assays. The basic principle is that the detection analyte is small and rotates rapidly (low polarization). When the detection analyte binds to the larger molecule (enzyme), its rotation slows down considerably (polarization changes from low to high polarization).

SUMMARY OF THE INVENTION

One exemplary embodiment may be directed to a fluorescence polarization assay, and associated method of use, that screens compounds or agents for their affinity to hematopoietic prostaglandin D synthase (H-PGDS) based on their ability to displace a fluorophore-containing detection analyte non-covalently bound to a protein comprising the primary amino acid sequence of H-PGDS.

Another exemplary embodiment may be directed to a fluorophore-containing detection analyte possessing a ligand component that binds to H-PGDS.

Another exemplary embodiment may be directed to a fusion enzyme comprising the primary amino acid sequence of H-PGDS and an added amino acid sequence that increases enzyme mass for the purpose of slowing molecular rotation without materially interfering with ligand binding at the H-PGDS active site.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

BRIEF DESCRIPTION OF THE DRAWINGS

FIG. 1 illustrates exemplary fluorophore coupling agents that may be used to prepare exemplary detection analytes;

FIG. 3 shows the primary amino acid sequence (SEQ ID NO: 3), in both one letter and three letter abbreviations, of the human H-PGDS enzyme (23 kDa) used in the exemplary embodiments;

FIG. 6 shows the primary amino acid sequence (SEQ ID NO: 2), in both one letter and three letter abbreviations, of the maltose binding protein (MBP)-H-PGDS fusion enzyme used in the exemplary embodiments;

DETAILED DESCRIPTION OF THE INVENTION

Figure 2:
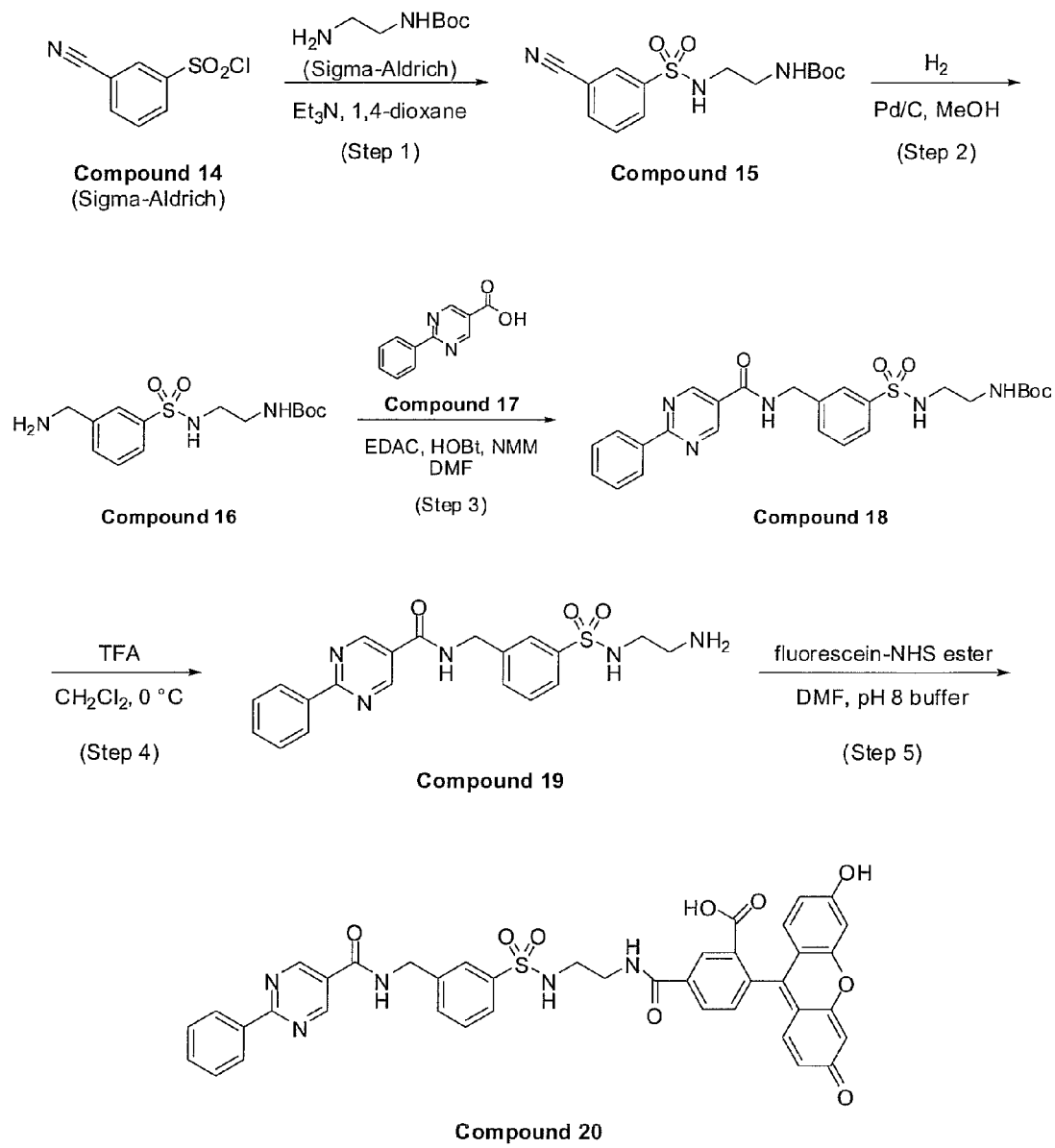
FIG. 2 outlines a general synthetic pathway for the detection analyte 2-(6-hydroxy-3-oxo-3H-xanthen-9-yl)-5-(2-(3-((2-phenylpyrimidine-5-carboxamido)methyl)phenylsulfonamido)ethylcarbamoyl)-benzoic acid.

The exemplary embodiments may be directed to a fluorescence polarization assay for identifying compounds or agents that possess binding affinity for H-PGDS, compounds or agents which may provide novel therapies for the treatment of allergic rhinitis, perennial rhinitis, rhinorrhea, nasal congestion, nasal inflammation, all types of asthma, COPD, allergic conjunctivitis, arthritis, atopic dermatitis and other types of dermal inflammation, ocular inflammation, wound healing, dermal scarring, multiple sclerosis, Alzheimer's disease, and disorders resulting from ischemia-reperfusion injury.

The exemplary embodiments herein may provide a homogenous, rapid and consistent assay for high-throughput screening of compounds or agents for H-PGDS affinity relative to a detection analyte that potently binds to H-PGDS.

One exemplary assay mixture for identifying compounds or agents that possess binding affinity for H-PGDS may include a detection analyte that binds to H-PGDS including a potent H-PGDS ligand component (an enzyme-binding compound) bound to a fluorophore (a fluorophore moiety), a cofactor such as glutathione, an enzyme that includes primary amino acid sequence of human recombinant H-PGDS, and the test compound or agent having an unknown binding affinity to H-PGDS. The exemplary assay mixture may also include an additional amino acid sequence to increase the mass of the enzyme for the purpose of slowing molecular rotation but without materially interfering with ligand binding at the H-PGDS active site.

Another exemplary embodiment may be directed to the enzyme that includes primary amino acid sequence of human recombinant H-PGDS that may be utilized in the exemplary assay mixture.

Still another exemplary embodiment may be directed to the enzyme that includes primary amino acid sequence of human recombinant H-PGDS and the additional amino acid sequence for increasing the mass of the enzyme as described above that may be utilized in the exemplary assay mixture.

Another exemplary embodiment may be directed toward the detection analyte.

The use of an unstable substrate such as prostaglandin $H_2$ ($PGH_2$), which is used in existing assays that measure H-PGDS activity, may therefore be obviated.

One exemplary method for identifying these compounds or agents includes first incubating an assay mixture including a detection analyte that binds to H-PGDS including a potent H-PGDS ligand component (an enzyme-binding compound) bound to a fluorophore (a fluorophore moiety), a cofactor such as glutathione, an enzyme including the primary amino acid sequence of human recombinant H-PGDS, and a test compound or agent. Next, the assay mixture may be excited with polarized electromagnetic radiation possessing an excitation wavelength. Next, the fluorescence polarization signal emitted by the assay mixture may be measured, from which the fluorescence polarization (mP) may be determined. Finally, the test compound or agent binding affinity ($IC_{50}$) may be determined by plotting the mP versus the test compound or agent concentration to generate a dose-response curve (i.e. the test compound or agent binding affinity is compared to a baseline signal generated and measured in exactly the same manner for an assay mixture without the test compound or agent).

The detection analyte, also called a fluorescent probe, comprises an enzyme-binding component and a fluorophore moiety. The detection analyte both binds with the enzyme in a competitive manner with the test compound or agent and fluoresces upon excitation with light that possesses its excitation wavelength. The enzyme-binding component may be any molecule that binds to the enzyme with such affinity as to cause a sufficient FP signal at relevant test concentrations.

One exemplary detection analyte enzyme-binding component may include the molecule N-substituted-2-phenylpyrimidine-5-carboxamide, whereas the N-substitution of the amide functional group may be any molecular arrangement that maintains or augments binding affinity potency of the detection analyte with the enzyme as to cause sufficient FP signal at relevant test concentrations. Preferred substitutions include but are not limited to benzyl, phenyl, phenethyl, 2-pyridyl, 3-pyridyl, and 4-pyridyl. Preferred sites of linkage with the fluorophore or with the linker moiety that connects the compound to the fluorophore include any open aromatic position on the N-substitution moiety. More preferred sites of linkage are an aromatic carbon atom of the N-substitution moiety meta to the 2-phenylpyrimidine-5-carboxamide portion of the compound.

Another exemplary detection analyte enzyme-binding component may include the molecule N-substituted-6-phenylnicotinamide, whereas the N-substitution of the amide functional group may be any molecular arrangement that maintains or augments binding affinity potency of the detection analyte with the enzyme as to cause sufficient FP signal at relevant test concentrations. Preferred substitutions may include but are not limited to benzyl, phenyl, phenethyl, 2-pyridyl, 3-pyridyl, and 4-pyridyl. Preferred sites of linkage with the fluorophore or with the linker moiety that may connect the compound to the fluorophore include any open aromatic position on the N-substitution moiety. More preferred sites of linkage may be an aromatic carbon atom of the N-substitution moiety meta to the 6-phenylnicotinamide portion of the compound.

Yet another exemplary detection analyte enzyme-binding component may include the molecule N-substituted-2-phenoxypyrimidine-5-carboxamide, whereas the N-substitution of the amide functional group may be any molecular arrangement that maintains or augments binding affinity potency of the detection analyte with the enzyme as to cause sufficient FP signal at relevant test concentrations. Preferred substitutions may include but are not limited to benzyl, phenyl, phenethyl, 2-pyridyl, 3-pyridyl, and 4-pyridyl. Preferred sites of linkage with the fluorophore or with the linker moiety that may connect the compound to the fluorophore include any open aromatic position on the N-substitution moiety. More preferred sites of linkage may be an aromatic carbon atom of the N-substitution moiety meta to the 2-phenoxypyrimidine-5-carboxamide portion of the compound.

Still another exemplary detection analyte enzyme-binding component may include the molecule N-substituted-6-phenoxynicotinamide, whereas the N-substitution of the amide functional group may be any molecular arrangement that maintains or augments binding affinity potency of the detection analyte with the enzyme as to cause sufficient FP signal at relevant test concentrations. Preferred substitutions may include but are not limited to benzyl, phenyl, phenethyl, 2-pyridyl, 3-pyridyl, and 4-pyridyl. Preferred sites of linkage with the fluorophore or with the linker moiety that may connect the compound to the fluorophore include any open aromatic position on the N-substitution moiety. More preferred sites of linkage may be an aromatic carbon atom of the N-substitution moiety meta to the 6-phenoxynicotinamide portion of the compound.

Another exemplary detection analyte enzyme-binding component may include the molecule N-substituted-4-(3-fluorobenzoyl)piperazine-1-carboxamide, whereas the N-substitution of the primary urea functional group may be any molecular arrangement that maintains or augments binding affinity potency of the detection analyte with the enzyme as to cause sufficient FP signal at relevant test concentrations. Preferred substitutions may include but are not limited to benzyl, phenyl, phenethyl, 2-pyridyl, 3-pyridyl, and 4-pyridyl. Preferred sites of linkage with the fluorophore or with the linker moiety that may connect the compound to the fluorophore include any open aromatic position on the N-substitution moiety. More preferred sites of linkage may be an aromatic carbon atom of the N-substitution moiety meta to the 4-(3-fluorobenzoyl)piperazine-1-carboxamide portion of the compound.

Another exemplary detection analyte enzyme-binding component may include the molecule 4-(5-benzoyl-1H-benzo[d]imidazol-2-yl)-N-substituted-3,5-dimethyl-1H-pyrrole-2-carboxamide, whereas the N— substitution of the amide functional group may be any molecular arrangement that maintains or augments binding affinity potency of the detection analyte with the enzyme as to cause sufficient FP signal at relevant test concentrations. Preferred substitutions may include but are not limited to benzyl, phenyl, phenethyl, 2-pyridyl, 3-pyridyl, and 4-pyridyl. Preferred sites of linkage with the fluorophore or with the linker moiety that may connect the compound to the fluorophore include any open aromatic position on the N-substitution moiety. More preferred sites of linkage may be an aromatic carbon atom of the N-substitution moiety meta to the 4-(5-benzoyl-1H-benzo[d]imidazol-2-yl)-3,5-dimethyl-1H-pyrrole-2-carboxamide portion of the compound.

Another exemplary detection analyte enzyme-binding component may include the molecule 5-(1-substituted-1H-pyrazol-3-yl)-2-phenylthiazole, whereas the N-substitution at the 1-position of the pyrazole ring may be any molecular arrangement that maintains or augments binding affinity potency of the detection analyte with the enzyme as to cause sufficient FP signal at relevant test concentrations. Preferred substitutions may include but are not limited to benzyl, phenyl, phenethyl, 2-pyridyl, 3-pyridyl, and 4-pyridyl. Preferred sites of linkage with the fluorophore or with the linker moiety that may connect the compound to the fluorophore include any open aromatic position on the N-substitution moiety. More preferred sites of linkage may be an aromatic carbon atom of the N-substitution moiety meta to the 5-(1H-pyrazol-3-yl)-2-phenylthiazole portion of the compound.

Another exemplary detection analyte enzyme-binding component may include the molecule 5-(2-substituted-imidazol-4-yl)-2-phenylpyrimidine, whereas the substitution at the 2-position of the imidazole ring may be any molecular arrangement that maintains or augments binding affinity potency of the detection analyte with the enzyme as to cause sufficient FP signal at relevant test concentrations. Preferred substitutions may include but are not limited to benzyl, phenyl, phenethyl, 2-pyridyl, 3-pyridyl, and 4-pyridyl. Preferred sites of linkage with the fluorophore or with the linker moiety that may connect the compound to the fluorophore include any open aromatic position on the N-substitution moiety. More preferred sites of linkage may be an aromatic carbon atom of the N-substitution moiety meta to the 5-(1H-pyrazol-3-yl)-2-phenylthiazole portion of the compound.

The fluorophore moiety may be a component, or functional group, of a molecule that absorbs light energy of a specific wavelength, called an excitation wavelength. Absorption of light at an excitation wavelength may cause the fluorophore to exist for a brief interval at a high-energy electronic state ($S_1$) relative to a ground state ($S_0$). A preferred range of excitation wavelengths for the detection analytes may be about 470-640 nanometers (nm). The fluorophore moiety subsequently may emit light energy at a different but equally specific wavelength in a de-excitation step, causing the molecule to fluoresce. A preferred range of emission wavelengths for the detection analytes may be about 500-700 nm (green-to-red visible light range). A more preferred range of emission wavelengths for the detection analytes may be about 600-700 nm (orange-to-red visible light range). The fluorescence lifetime may be the brief interval (measured on the nanosecond, or $10^{-9}$ to $10^{-7}$, timescale) in which a fluorophore exists in its excited state prior to its de-excitation to the ground state. Exemplary fluorophores include but are not limited to fluorescein, tetramethyl rhodamine, 5-carboxy-X-rhodamine, Texas Red, and DyLight™ 633. Table 1 lists these exemplary fluorophores, each with its excitation wavelength, emission wavelength, and emission color.

TABLE 1

| Fluorophore | Excitation Wavelength | Emission Wavelength | Emission Color |
|---|---|---|---|
| Fluorescein | 495 nm | 520 nm | Green |
| Tetramethyl rhodamine | 550 nm | 570 nm | Yellow |
| 5-Carboxy-X-rhodamine (5-ROX) | 567 nm | 591 nm | Orange |
| Texas Red (TR) | 596 nm | 620 nm | Red |
| DyLight™ 633 | 638 nm | 658 nm | Red |

Preferred exemplary embodiments may utilize detection analytes with fluorophores that possess emission wavelengths sufficiently different from the wavelengths of background polarized light that may be emitted as a result of the assay mixture excitation step as to maximize measurement of FP signal produced by the fluorophore component enzyme-bound detection analyte.

The compound or agent component of the detection analyte may be linked with the fluorophore moiety through a direct chemical bond. The detection analyte may further comprise a linker moiety that chemically bridges the compound or agent with the fluorophore. Exemplary linker moieties may include but are not limited to:

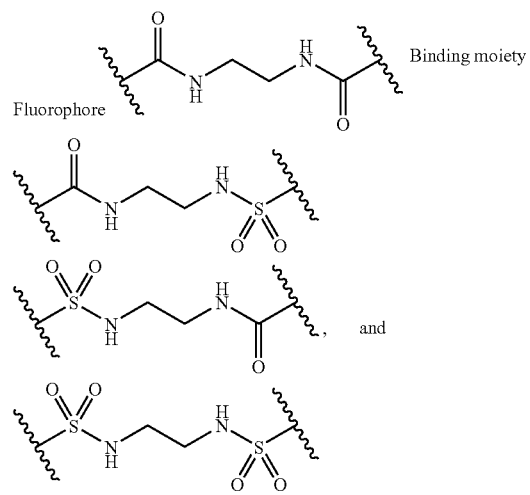

In one exemplary embodiment, the detection analyte may be 2-(6-hydroxy-3-oxo-3H-xanthen-9-yl)-5-(2-(3-((2-phenylpyrimidine-5-carboxamido)methyl)phenylsulfonamido)ethylcarbamoyl)benzoic acid (Example 6, Compound 20).

In another exemplary embodiment, the detection analyte may be N-(3-(N-(2-(5-carbonyl-X-rhodamine)amino)ethyl)sulfamoyl)benzyl)-2-phenylpyrimidine-5-carboxamide (Example 7, Compound 21).

In yet another exemplary embodiment, the detection analyte may be N-(3-(N-(2-(DyLight™633)amino)ethyl)sulfamoyl)benzyl)-2-phenylpyrimidine-5-carboxamide (Example 8, Compound 22).

In yet another exemplary embodiment, the enzyme may include a primary amino acid sequence of a hematopoietic prostaglandin D synthase (H-PGDS). Exemplary embodiments may include a wild-type H-PGDS, otherwise referred to hereinafter as a fusion enzyme. Exemplary fusion enzymes may more specifically include human wild-type H-PGDS. The fusion enzyme may further include a polyhistidine tag at or near the N-terminus of the enzyme, as shown in FIG. 3. Exemplary fusion enzymes may include a hexahistidine tag (SEQ ID NO: 1) inserted between the first residue (methionine) and the second residue (proline) of human wild-type H-PGDS.

Another exemplary embodiment of the fusion enzyme includes the primary amino acid sequence of a hematopoietic prostaglandin D synthase (H-PGDS) and an amino acid sequence that may add mass to the enzyme for the purpose of slowing molecular rotation (tumbling) but does not materially interfere with ligand binding at the H-PGDS active site. An exemplary fusion enzyme includes a maltose binding protein (MBP) amino acid sequence fused with the N-terminus of the H-PGDS, as shown in FIG. 6.

Figure 4:
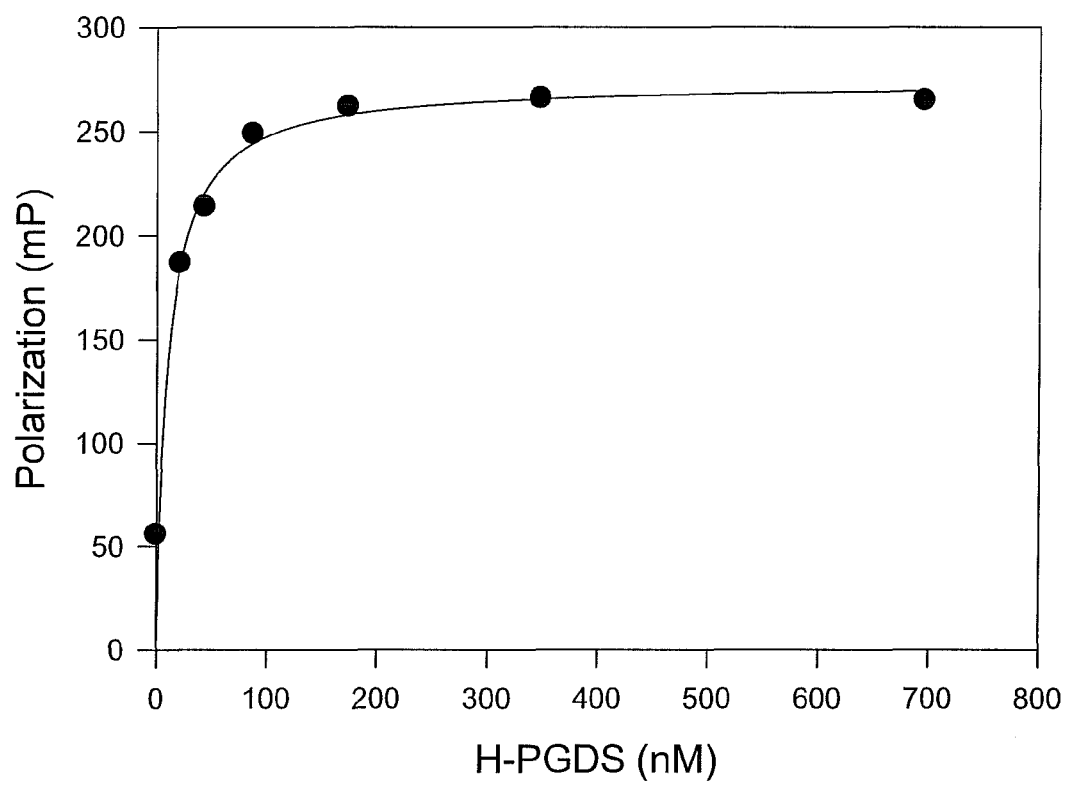
FIG. 4 is a plot showing increasing polarization (mP) signal with increasing H-PGDS enzyme (23 kDa) concentration at the constant detection analyte (Compound 20) concentration.

In another exemplary embodiment, the assay may utilize the enzyme with a concentration from 1 nM to 1000 nM, as shown in FIG. 4, in order to produce a useful FP signal.

Figure 5:
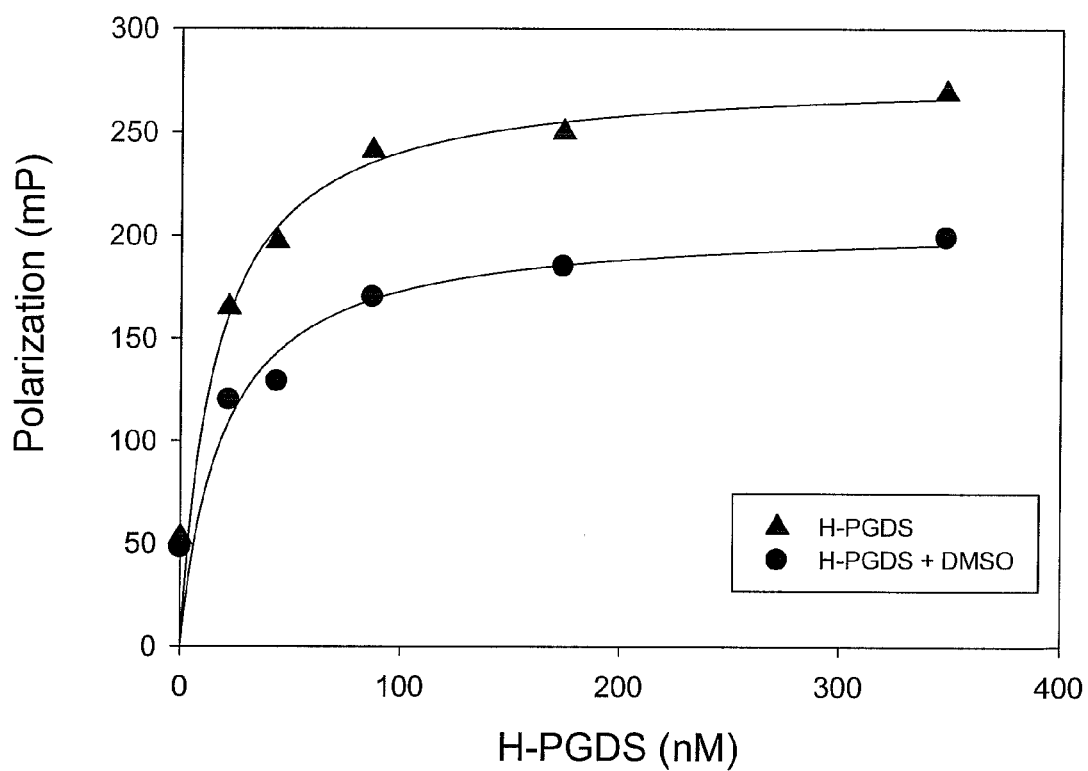
FIG. 5 is a plot showing the effect of 5% DMSO on the polarization (mP) signal versus H-PGDS enzyme (23 kDa) concentration.
Figure 7:
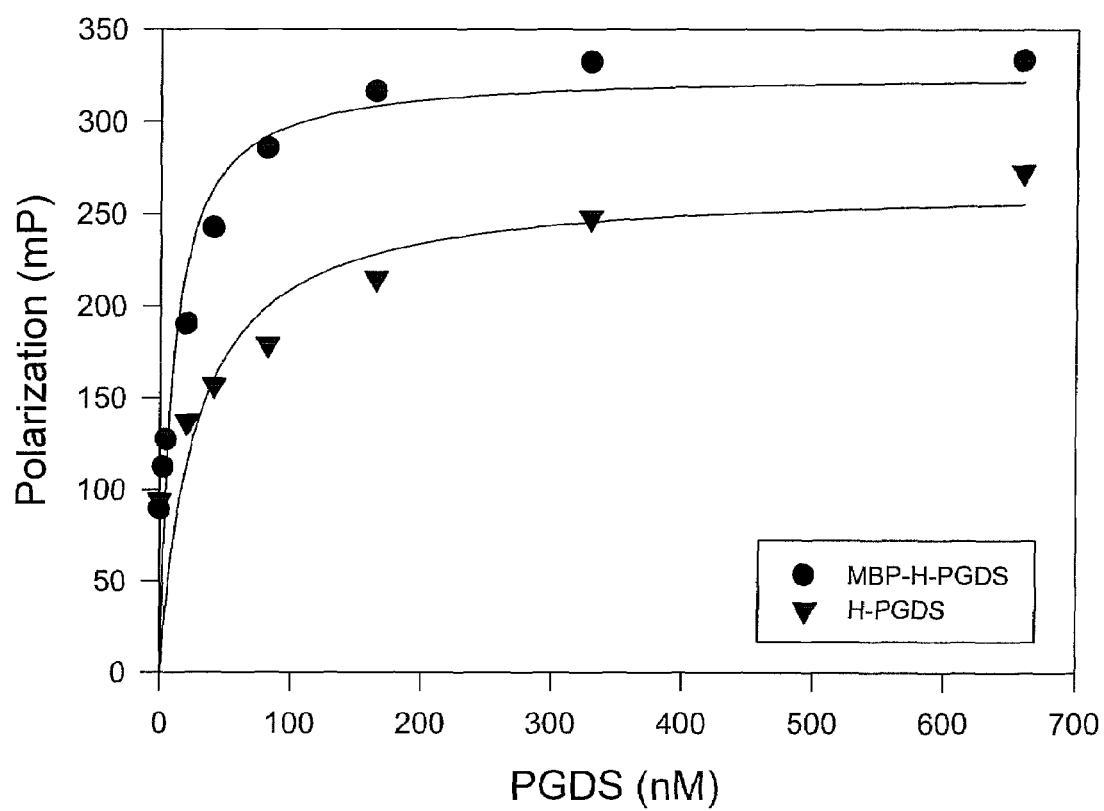
FIG. 7 is a plot showing increasing polarization (mP) signal with increasing MBP-H-PGDS fusion enzyme (66 kDa) concentration compared to increasing mP signal with increasing H-PGDS enzyme (23 kDa) concentration.
Figure 8:
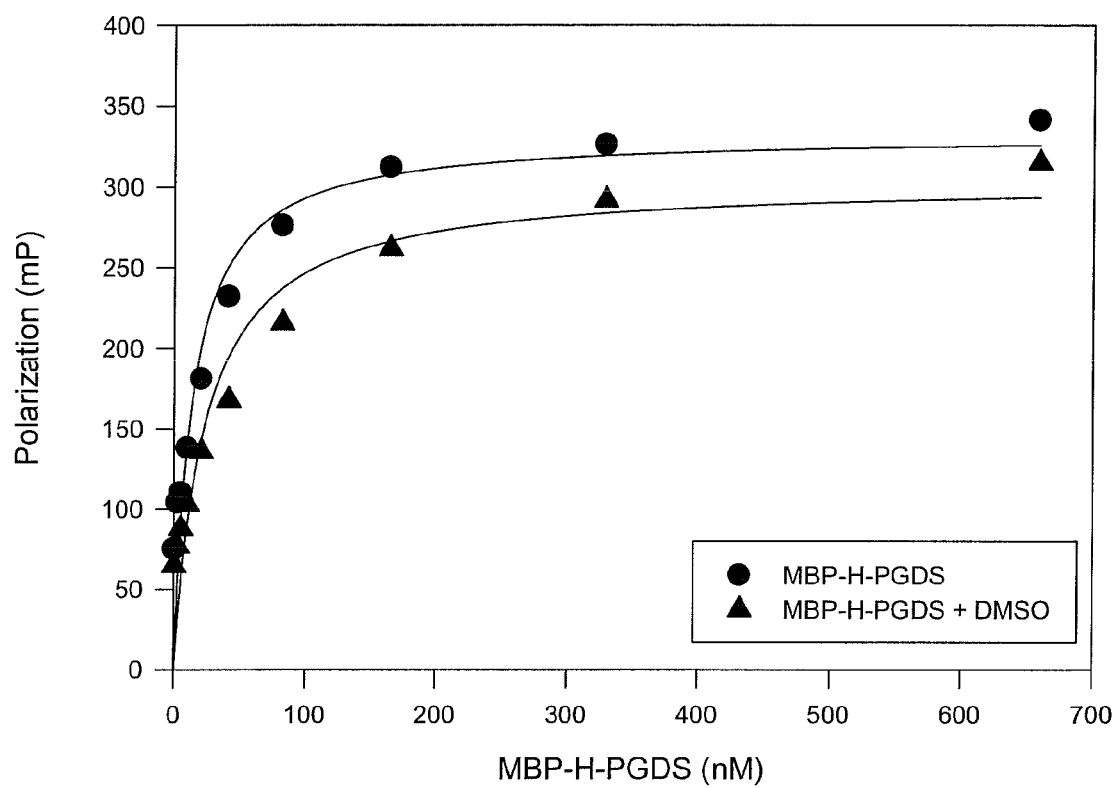
FIG. 8 is a plot showing the effect of 5% DMSO on the polarization (mP) signal versus MBP-H-PGDS fusion enzyme (66 kDa) concentration.
Figure 9:
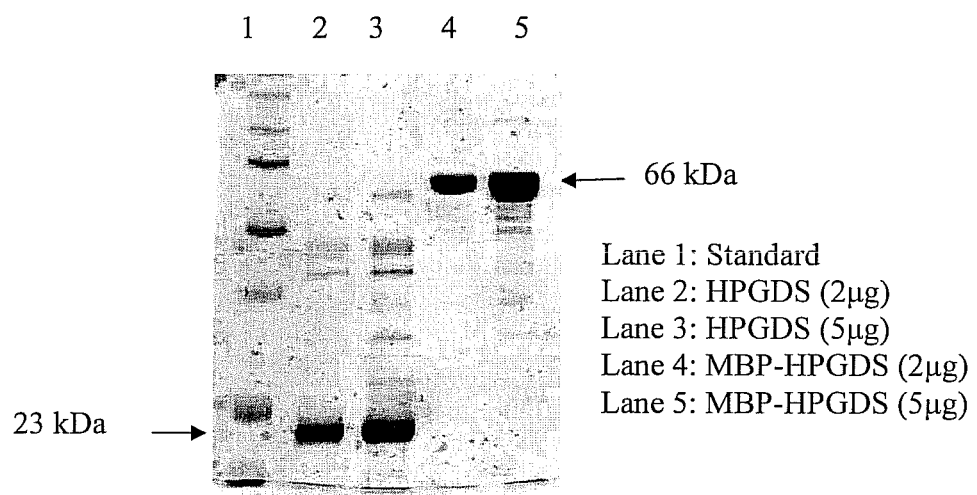
FIG. 9 illustrates a coomassie stained 12% SDS-PAGE of purified H-PGDS enzyme (23 kDa) and MBP-H-PGDS fusion enzyme (66 kDa) demonstrating the difference in size between the two enzymes.
Figure 10:
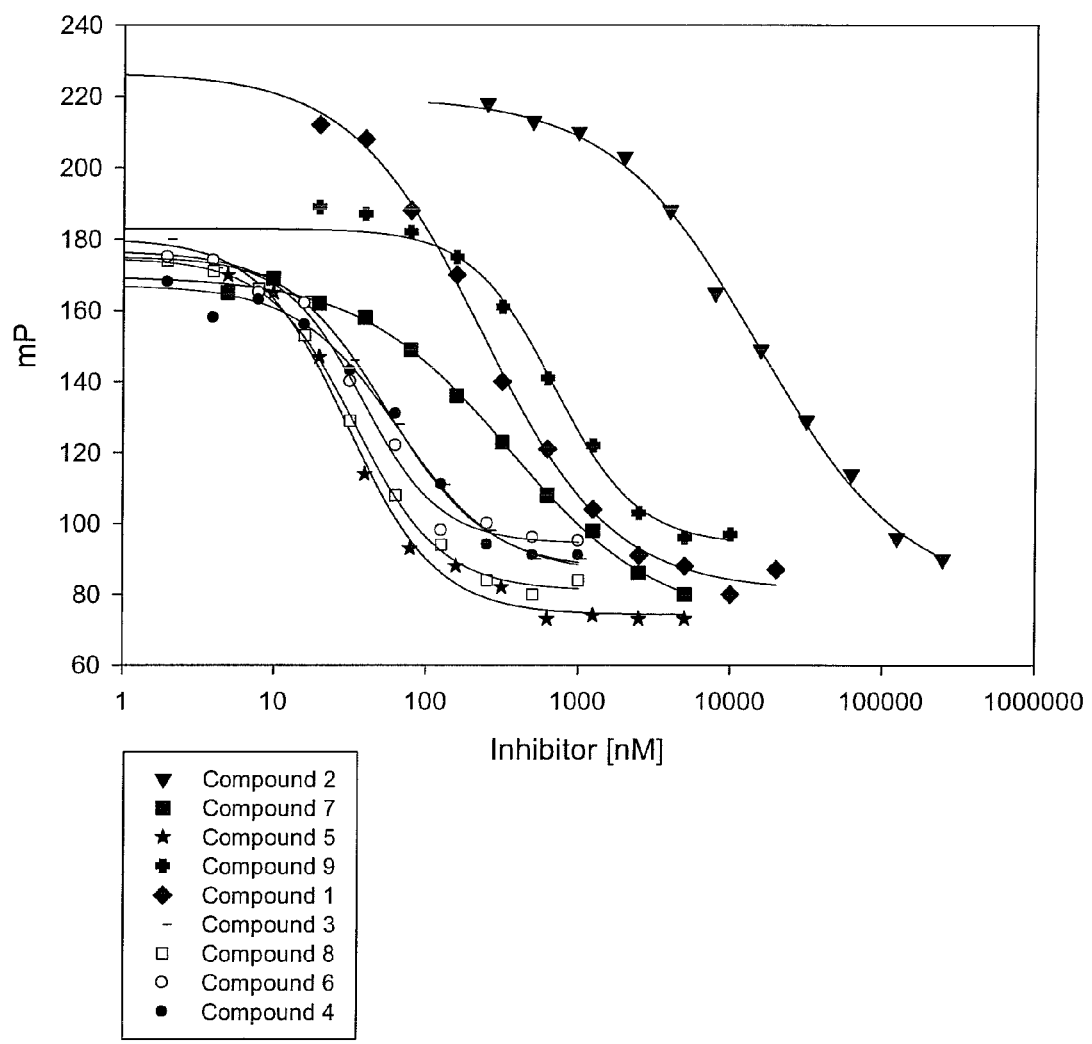
FIG. 10 plots titration curves produced by the testing of nine known H-PGDS inhibitors in the H-PGDS FP assay showing the ability of the assay to identify binders of various potencies.
Figure 11:
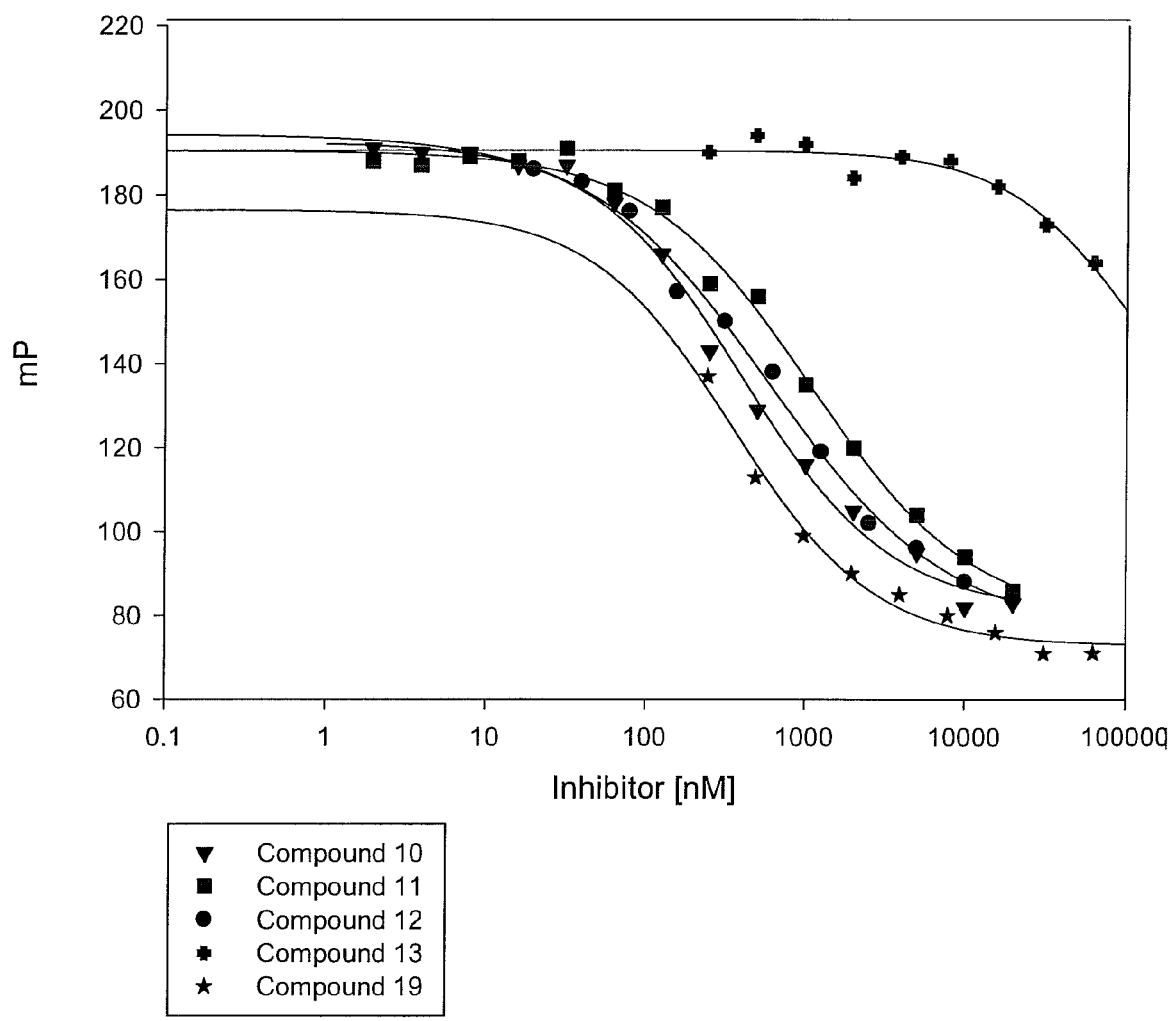
FIG. 11 plots titration curves for novel H-PGDS inhibitors.

In still another exemplary embodiment, the assay may further utilize DMSO as a cosolvent at zero to ten volume percent with water or an aqueous buffer solution, or another cosolvent such as ethanol or methanol used with water or an aqueous buffer solution that would not compromise the FP signal and so that compounds could be screened from picomolar to micromolar concentration ranges, as shown in FIGS. 5 and 8.

In another exemplary embodiment, the assay may further employ an incubation time of the detection analyte with the enzyme from about five to 120 minutes.

In another exemplary embodiment, the assay may further utilize glutathione (GSH) as a cofactor with a concentration from about 0.1 mM to 10 mM.

In another exemplary embodiment, the assay may further utilize a buffer solution in the pH range of about 6.6 to 8.5 from the group including Tris, HEPES, phosphate, MOPS, Bis-Tris, and Tris-HCl.

In another exemplary embodiment, the assay may utilize one or more salt additives such as sodium chloride or potassium chloride in the concentration ranging from about 10 mM to 500 mM.

In another exemplary embodiment, the assay may utilize a detergent additive such as CHAPS with a concentration from about 0.1 mM to 10 mM.

In another exemplary embodiment, the assay may utilize a reducing agent such as DTT, β-ME, or TCEP with a concentration from about 0.1 mM to 10 mM.

In another exemplary embodiment, the assay may utilize a black non-binding plate surface.

When used in the present application, the following abbreviations have the meaning set out below:
Ac is acetyl;
β-ME is beta-mercaptoethanol;
Boc is butyloxycarbonyl;
BSA is bovine serum albumin;
CHAPS is 3-[(3-cholamidopropyl)dimethylammonio]-propanesulfonic acid;
$CH_2Cl_2$ is dichloromethane;
$CH_3CN$ is acetonitrile;
$CDCl_3$ is deuterochloroform;
DCC is N,N'-dicyclohexylcarbodiimide;
DME is 1,2-dimethoxyethane;
DMF is N,N-dimethylformamide;
DMSO is dimethyl sulfoxide;
DTT is dithiothreitol;
EDAC is N-(3-dimethylaminopropyl)-N'-ethylcarbodiimide hydrochloride;
EDTA is ethylenediaminetetraacetic acid;
EIA is enzyme immunoassay;
Et is ethyl;
$Et_3N$ is triethylamine;
HCl is hydrogen chloride;
HEPES is 4-(2-hydroxyethyl)-1-piperazineethanesulfonic acid;
HOBt is 1-hydroxybenzotriazole;
Me is methyl;
MeOH is methanol;
MOPS is 3-(N-morpholino)propanesulfonic acid;
$NaN_3$ is sodium azide;
NHS is N-hydroxysuccinimide;
NMM is N-methylmorpholine;
Pd/C is palladium on carbon;
Ph is phenyl;
RT or rt is room temperature;
TCEP is tris(2-carboxyethyl)phosphine hydrochloride;
TFA is trifluoroacetic acid; and
Tris-HCl is 2-amino-2-(hydroxymethyl)-1,3-propanediol hydrochloride.

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well known and commonly used in the art.

The above description of embodiments of the invention is merely exemplary in nature and, thus, variations thereof are not to be regarded as a departure from the spirit and scope of the invention.

EXAMPLES

Mass spectra (MS) were obtained using a Finnigan MAT LCQ mass spectrometer (classic, serial number is LC000930).

Nuclear magnetic resonance (NMR) spectra were obtained using either a Bruker (300 MHz) or a Varian INOVA (400 MHz) nuclear magnetic resonance spectrometer.

High performance liquid chromatography (HPLC) analytical separations were performed on an Agilent 1100 HPLC and followed by an Agilent Technologies G1315B Diode Array Detector with $UV_{max}$ @ 633 nm.

Example 1

Fluorescence Polarization Assay

Detection analyte and H-PGDS-MBP fusion enzyme were incubated in the presence of reduced glutathione (5 mM) for 30-60 minutes at room temperature and FP was measured using a TECAN SAFIRE 2 plate reader equipped with absorbance, fluorescence, fluorescence polarization and FRET capabilities. Assays were performed in 96-well microtiter plates in 100 μL of total sample volume. Excitation and emission wavelengths appropriate for the employed detection analyte were used.

Step 1: Preparation of Reagents (a). Detection Analyte: H-PGDS FP Fluorescent Probe—Green FP buffer concentrate (4×(200 mM Tris pH8.0, 200 mM KCl, 20 mM CHAPS, 40 mM DTT), Cayman Chemical Catalog No. 600028, 6 mL) was diluted with deionized water (18 mL) to provide 1×FP buffer (24 mL).

A solution consisting of 2-(6-hydroxy-3-oxo-3H-xanthen-9-yl)-5-(2-(3-((2-phenylpyrimidine-5-carboxamido)methyl)phenylsulfonamido)ethylcarbamoyl)benzoic acid (Compound 20, see Example 6, 2 μg) in absolute ethanol (20 μL, 100 μg/mL) was diluted with 1×FP buffer (180 μL) to provide the H-PGDS FP fluorescent probe—green reagent.

(b). Enzyme: MBP-H-PGDS Fusion

H-PGDS-Maltose binding protein (MBP; 100 μl, 0.5 mg/ml) fusion (MBP-H-PGDS fusion) (FIG. 6) was diluted with 1×FP buffer (900 μL).

(c). HQL-79 FP Positive Control

Twelve clean microfuge tubes were labeled A1 through A12. A 5 mM 4-(diphenylmethoxy)-1-[3-(1H-tetrazol-5-yl)propyl-piperidine (HQL-79) in dimethyl sulfoxide (DMSO) solution (Cayman Chemical Catalog No. 600027, 100 μL) was added to tube A12. Dimethyl sulfoxide (50 μL) was added to each of tubes A1 through A11. The HQL-79 control solution was serially diluted by removing 50 μL from tube A12 and placing it in tube A11 with subsequent thorough mixing of the contents of tube A11. Next, 50 μL was removed from tube A11 and was placed into tube A10 with subsequent thorough mixing of the contents of tube A10. This process was repeated for tubes A9 through A2.

(d). Glutathione (GSH) Solution

A 100 mM aqueous (deionized water) glutathione solution (1,500 µL in vial) was obtained from Cayman Chemical Company (Catalog No. 600029).

Step 2: Preparation of Assay Cocktail

Into a 50 mL conical tube was added the H-PGDS 1×FP buffer (18.65 mL), H-PGDS FP fluorescent probe—green (138 µL), MBP-H-PGDS fusion dilution (880 µL), and glutathione solution (1,250 µL). The cocktail prepared was enough for either a standard 96-well, 384-well, or higher density plate.

Step 3: Preparation of Test Compound Solutions

A test compound may be dissolved in DMSO, ethanol, or methanol at several concentrations when the titration endpoint is unknown. A final volume of 2.5 µL is added to each inhibitor well.

Step 4: Assay Protocol (384-Well Plate Format)

(a). Apportionment of the Assay Cocktail

Assay cocktail (47.5 µL) was added to each plate well.

(b). Preparation of Maximum Binding (100% Activity) Wells

DMSO (2.5 µL) from microfuge tube A1 was added to each plate well A1 and B1.

(c). Apportionment of HQL-79 Positive Control Solution

Positive control solution (2.5 µL) from microfuge tube A2 was added to each plate well A2 and B2. Positive control solution (2.5 µL) from microfuge tube A3 was added to each plate well A3 and B3. This procedure was continued until all the positive control standard dilutions were aliquoted.

(d). Apportionment of Test Compound Solutions

Test compound solutions (2.5 µL) were added to the wells. Each test compound concentration was typically assayed in duplicate or triplicate. The $IC_{50}$ for a particular test compound was obtained by performing a full concentration titration versus a full concentration titration of positive control. Comparison of a single concentration of a test compound to the maximum binding well provided an assessment of the relative affinity of the test compound for MBP-H-PGDS.

(e). Incubation

The plate was covered and incubated for 60-90 minutes at room temperature. The FP signal is stable for at least two hours.

(f). Plate Reading

Plates were read with excitation and emission wavelengths of 470 nm and 530 nm (for detection analyte comprising the fluorescein fluorophore), respectively. The measurements were taken in the fluorescent polarization mode with the z-height set to the middle of the well and the G-factor set to 1.13 on a Tecan Safire 2 reader.

Step 5: Analysis (See Note in Step 4 Above)

(a). Calculations fluorescence polarization of a molecule is defined as:

$$\text{Polarization (mP)} = 1{,}000 \times (I_{parallel} - I_{perpendicular})/(I_{parallel} + I_{perpendicular})$$

where $I_{parallel}$ is the parallel emission intensity measurement and $I_{perpendicular}$ is the perpendicular emission intensity measurement.

A plot of mP versus test compound concentration on semi-log axes resulted in a sigmoidal dose-response curve typical of competitive binding assays. This data can be fit to a 4-parameter logistic equation.

When full titration curves were performed, the concentration of test compound that reduced the mP signal by 50% ($IC_{50}$) was estimated from a graph for each test compound tested.

If a test compound is tested at only one or two concentrations, an estimate of relative efficacy can be determined using the following equation:

$$\% \text{ Signal Reduction} = 100 \times (\text{mP 100\% Activity} - \text{mP Sample})/(\text{mP 100\% Activity})$$

B. Performance Characteristics: Z'-Factor

Z'-factor is a term used to describe the quality of an assay (Hohwy, M., Spadola, L., Lundquist, B. et al., *J. Medicinal Chem.*, 2008, 51(7), 2178-2186), which is calculated using the following equation:

$$Z' = 1 - [(3\sigma_{C+} + 3\sigma_{C-})/|\mu_{C+} - \mu_{C-}|]$$

Figure 12:
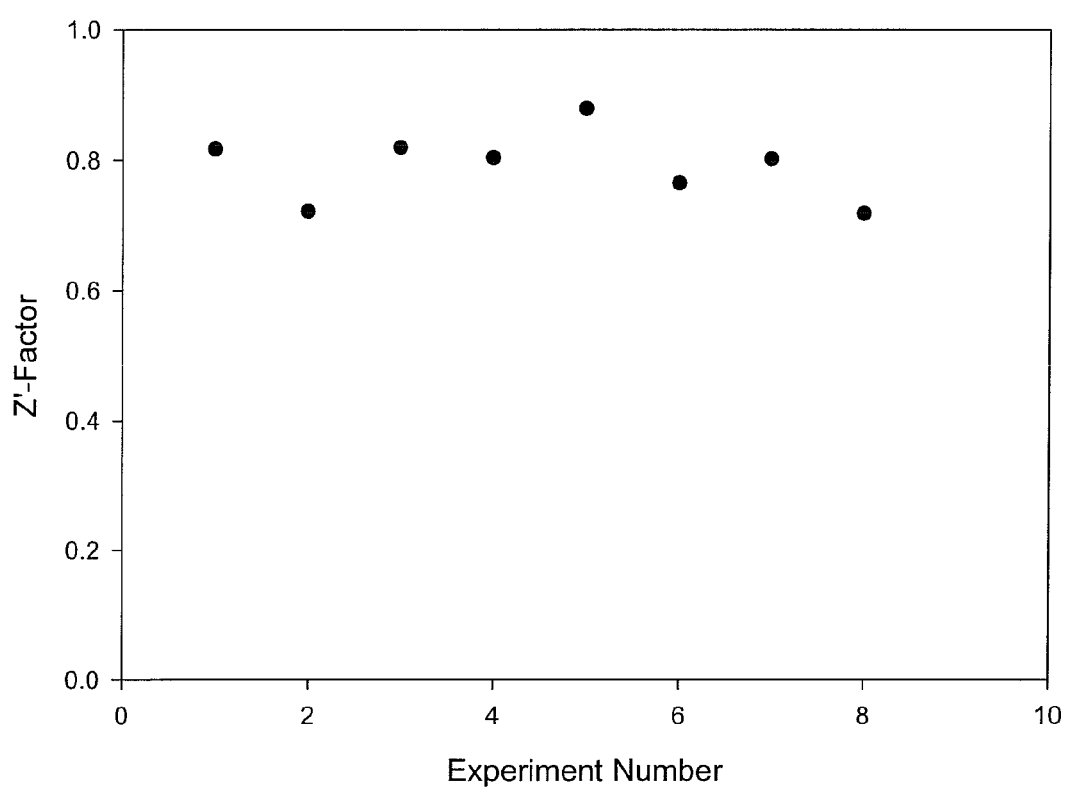
FIG. 12 shows the performance characteristics of the FP binding assay.

The Z'-factor is computed from four parameters: the means and standard deviations of both the positive (C+) and negative (C−) controls ($\mu_{C+}, \sigma_{C+}$ and $\mu_{C-}, \sigma_{C-}$). The theoretical upper limit for the Z'-factor is 1.0. A robust assay has a Z'-factor >0.5 (Zhang, J. H., Chung, T. D. Y., and Oldenburg, K. R. *J. Biomolecular Screening*, 1999, 4(2), 67-73). The Z'-factor for this assay using the fluorescent probe—green as described in this example was determined to be 0.79 (FIG. 12). Other detection analytes (fluorescent probes) may be used interchangeably according to the desire to avoid interference between emission wavelength/color with background light. Table 2 below records test data for various compounds screened using the disclosed method of Example 1.

TABLE 2

| H-PGDS Inhibitor | Detection Analyte | MBP-H-PGDS FP Assay: test compound $IC_{50}$ (nM) | Reported H-PGDS inhibition $IC_{50}$ (nM) |
| --- | --- | --- | --- |
| N-benzyl-2-phenylpyrimidine-5-carboxamide[a]<br>Compound 1 | Compound 20 | 125 ± 0<br>(N = 2) | 10[a] |

TABLE 2-continued

| H-PGDS Inhibitor | Detection Analyte | MBP-H-PGDS FP Assay: test compound IC$_{50}$ (nM) | Reported H-PGDS inhibition IC$_{50}$ (nM) |
| --- | --- | --- | --- |
| 1-(3-(1H-tetrazol-5-yl)propyl)-4-(benzhydryloxy)piperidine (HQL-79)[b]<br>Compound 2 | Compound 20 | 15000 ± 0<br>(N = 2) | 6000[b] |
| N-(1-benzylpiperidin-4-yl)-2-phenylpyrimidine-5-carboxamide[c]<br>Compound 3 | Compound 20 | 50 ± 14<br>(N = 2) | 0.428[c] |
| N-(1-benzylpiperidin-4-yl)-6-phenylnicotinamide[d]<br>Compound 4 | Compound 20 | 30<br>(N = 1) | 1.57[d] |
| N-(1-benzylpiperidin-4-yl)-6-(3-fluorophenyl)nicotinamide[e]<br>Compound 5 | Compound 20 | 30 ± 0<br>(N = 2) | 0.946[e] |

TABLE 2-continued

| H-PGDS Inhibitor | Detection Analyte | MBP-H-PGDS FP Assay: test compound IC$_{50}$ (nM) | Reported H-PGDS inhibition IC$_{50}$ (nM) |
| --- | --- | --- | --- |
| N-(4-morpholinophenyl)-2-phenoxypyrimidine-5-carboxamide[f]<br>Compound 6 | Compound 20 | 38 ± 11<br>(N = 2) | 190[f] |
| 4-(3-fluorobenzoyl)-N-(6-methylbenzo[d]thiazol-2-yl)piperazine-1-carboxamide[g]<br>Compound 7 | Compound 20 | 308 ± 11<br>(N = 2) | 1-10[g] |
| 4-(5-benzoyl-1H-benzo[d]imidazol-2-yl)-3,5-dimethyl-N-(2-(22yridine-2-yl)ethyl)-1H-pyrrole-2-carboxamide[h]<br>Compound 8 | Compound 20 | 25 ± 7<br>(N = 2) | 72[h] |

TABLE 2-continued

| H-PGDS Inhibitor | Detection Analyte | MBP-H-PGDS FP Assay: test compound IC$_{50}$ (nM) | Reported H-PGDS inhibition IC$_{50}$ (nM) |
| --- | --- | --- | --- |
| 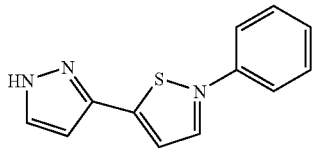<br>2-phenyl-5-(1H-pyrazol-3-yl)thiazole[f]<br>Compound 9 | Compound 20 | 438 ± 265<br>(N = 2) | 21[i] |
| 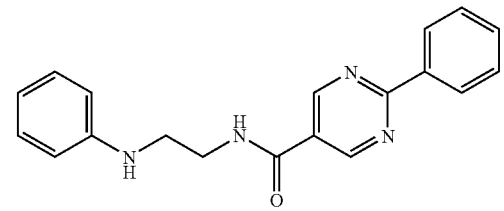<br>2-phenyl-N-(2-(phenylamino)ethyl)pyrimidine-<br>5-carboxamide<br>Compound 10 | Compound 20 | 375 ± 180<br>(N = 2) | N/A |
| 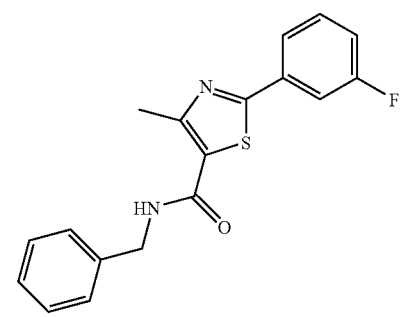<br>N-benzyl-2-(3-fluorophenyl)-4-methylthiazole-<br>5-carboxamide<br>Compound 11 | Compound 20 | 900 ± 140<br>(N = 2) | N/A |
| 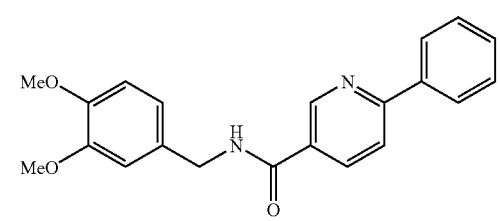<br>N-(3,4-dimethoxybenzyl)-6-phenylnicotinamide<br>Compound 12 | Compound 20 | 575 ± 460<br>(N = 2) | N/A |

TABLE 2-continued

| H-PGDS Inhibitor | Detection Analyte | MBP-H-PGDS FP Assay: test compound IC$_{50}$ (nM) | Reported H-PGDS inhibition IC$_{50}$ (nM) |
|---|---|---|---|
| 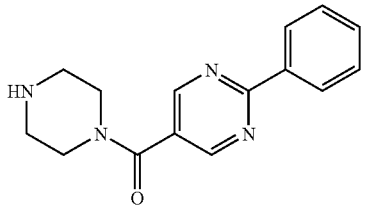(2-phenylpyrimidin-5-yl)(piperazin-1-yl)methanone Compound 13 | Compound 20 | 250000 (N = 1) | N/A |

[a] WO 2007/041634 to Aldous et al., entitled "Pyrimidine Amide Compounds as PGDS Inhibitors", Example 1; Inhibition of PGH$_2$ → PGD$_2$, EIA assay (Cayman Chemical, Catalog No. 500151 (Publication Data: May 14, 2003) to measure PGD$_2$ levels (Aventis)
[b] Aritake, K., Kado, Y., Inoue, T., Miyano, M., Urade, Y., J. Biol. Chem., 2006, 281(22), 15277-15286; Inhibition of [1-$^{14}$C]PGH$_2$ → [1-$^{14}$C]PGD$_2$, RIA assay (Osaka Bioscience Institue)
[c] WO 2008/104869 to Blake et al., entitled "Nicotinamide Derivatives as Inhibitors of H-PGDS and Their Use for Treating Prostaglandin D2 Mediated Diseases", Example 12; Inhibition of PGH$_2$ → PGD$_2$, fluorescence intensity assay (U.S. Pat. No. 2004/152148 to Lambalot, entitled ") to measure remaining PGH$_2$ levels by Fe(II) reduction of PGH$_2$ to malondialdehyde (MDA) and formation of fluorescent complex 2-thiobarbituric acid (TBA)-MDA (Pfizer)
[d] WO 2008/075172 to Blake et al., entitled "Nicotinamide Derivatives", Example 8; Inhibition of PGH$_2$ → PGD$_2$, fluorescence intensity assay (U.S. Pat. No. 2004/15248 by Lambalot) (Pfizer)
[e] WO 2008/075172 to Blake et al., entitled "Nicotinamide Derivatives", Example 29; Inhibition of PGH$_2$ → PGD$_2$, fluorescence intensity assay (U.S. Pat. No. 2004/152148 by Lambalot) (Pfizer)
[f] Abstract MEDI 26 (poster) Division of Medicinal Chemistry, American Chemical Society National Meeting, New Orleans, LA, April 6-10, 2008; Example 36 (Taiho)
[g] WO 2008/122787 to Babette et al., entitled "Piperazine Compounds for Inhibition of Haematopoietic D Synthetase", Example 80; GSH-MCB conjugation measured by fluorometry (Evotec)
[h] U.S. Pat. App. No. 2006/267454 to Keiko et al., entitled "Benzoimidazole Compound Capable of Inhibitin Prostaglandin D Synthetase, Example 34 (Taiho)
[i] Hohwy, M., Spadola, L., Lundquist, B. et al., J. Medicinal Chem., 2008, 51(7), 2178-2186; Compound 13; GSH-MCB conjugation measured by fluorometry (AstraZeneca)

Example 2

Preparation of 2-phenyl-N-(2-(phenylamino)ethyl) pyrimidine-5-carboxamide (Compound 10)

To a stirring mixture consisting of 2-phenylpyrimidine-5-carboxylic acid (Compound 17; synthesis described in Example 1, Steps 1-3 of WO 2007/041634 to Aldous et al., entitled "Pyrimidine Amide Compounds as PGDS Inhibitors"; 200 mg) in N,N-dimethylformamide (15 mL) was added successively N-methylmorpholine (Aldrich, 0.33 mL), N-phenethylenediamine (Acros, 173 mg), 1-hydroxybenzotriazole (209 mg), and 1-(3-dimethylamino-propyl)-3-ethylcarbodiimide hydrochloride (EDAC, 227 mg). The reaction mixture was stirred overnight under an argon atmosphere and was subsequently concentrated slightly under reduced pressure. The concentrate was partitioned between ethyl acetate (200 mL) and saturated aqueous sodium bicarbonate (200 mL). The layers were separated and the organic phase was washed twice with water (2×200 mL) and once with brine solution (200 mL), was dried over anhydrous magnesium sulfate, filtered, and concentrated under reduced pressure to give an off-white solid. Trituration with a small amount of absolute ethanol at room temperature, collection by vacuum filtration, and suction drying afforded the title compound as a white powder (0.230 g, 72.3% yield); 1H-NMR (300 MHz; CDCl$_3$) δ 9.13 (s, 2H), 8.51 (dd, 2H), 7.61-7.51 (m, 3H), 7.21 (t, 2H), 6.79 (t, 1H), 6.70 (d, 2H), 6.57 (broad m, 1H), 3.99 (broad m, 1H), 3.75 (m, 2H), 3.48 (t, 2H); MS (APCl$^+$) m/z 319.

Example 3

Preparation of N-benzyl-2-(3-fluorophenyl)-4-methylthiazole-5-carboxamide (Compound 11)

Step 1: Preparation of N-benzyl-2-bromo-4-methylthiazole-5-carboxamide

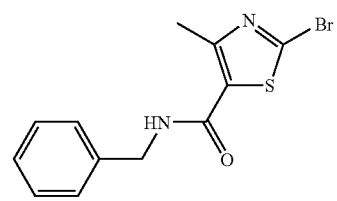 [SMILES: Cc1nc(Br)sc1C(=O)NCc1ccccc1]

To a mixture consisting of 2-bromo-4-methylthiazole-5-carboxylic acid (Sigma-Aldrich, 1.0 g), 1-(3-dimethylaminopropyl)-3-ethylcarbodiimide (EDC, 1.3 g), 1-hydroxybenzotriazole (0.613 g), N-methyl-2-pyrrolidinone (0.48 mL) in N,N-dimethylformamide was added a mixture consisting of benzylamine (0.54 mL) in N,N-dimethylformamide (5 mL). The reaction mixture was stirred overnight at room temperature and was subsequently partitioned between ethyl acetate (200 mL) and water (200 mL). The layers were separated and the organic phase was further washed twice with water (2×200 mL) and brine solution (150 mL), was dried over anhydrous sodium sulfate, filtered, and concentrated under reduced pressure afforded the title intermediate as a crude yellow oil (1.847 g; major spot R$_f$ 0.45 with 3:1 v/v hexanes-ethyl acetate solvent system) that solidified on standing at room temperature; MS (ESI$^-$) m/z 311.

Step 2: Preparation of N-benzyl-2-(3-fluorophenyl)-4-methylthiazole-5-carboxamide (Compound 11)

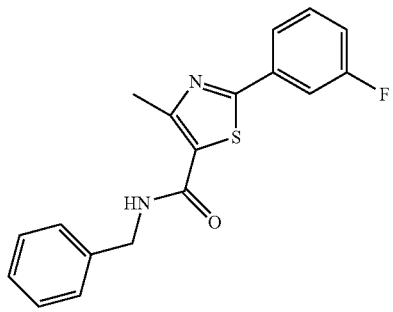 [SMILES: Cc1nc(-c2cccc(F)c2)sc1C(=O)NCc1ccccc1]

A mixture consisting of N-benzyl-2-bromo-4-methylthiazole-5-carboxamide (0.45 g), 3-fluorophenylboronic acid (0.40 g), tetrakis(triphenylphosphine)palladium(0) (0.16 g), N,N-dimethylformamide (15 mL), and a 2 M aqueous cesium carbonate solution (2.5 mL) was stirred at 90° C. under a nitrogen atmosphere for 2.5 hours. After cooling to room temperature, the mixture was partitioned between ethyl acetate (200 mL) and water (200 mL). The phases were separated and the organic phase was subsequently washed with a fresh portion of ether (200 mL) and brine solution (150 mL), was dried over anhydrous magnesium sulfate, and concentrated under reduced pressure to give a dark brown solid (0.89 g). The product was purified by flash silica column chromatography. Elution through a 12-g Silicycle® flash silica cartridge with a gradient of 5% to 10% ethyl acetate in hexanes afforded the title compound as a white solid (0.33 g, 70% yield); $R_f$ 0.68 with 7:3 v/v hexanes-ethyl acetate; $^1$H-NMR (300 MHz; CDCl$_3$) δ 7.77-7.60 (m, 2H), 7.47-7.30 (m, 6H), 7.16 (ddd, 1H), 6.10 (broad t, 1H), 4.64 (d, 2H), 2.78 (s, 3H); MS (ESI$^-$) m/z 325 (M−1).

Example 4

Preparation of N-(3,4-dimethoxybenzyl)-6-phenylnicotinamide (Compound 12)

Step 1: Preparation of 6-bromo-N-(3,4-dimethoxybenzyl)nicotinamide

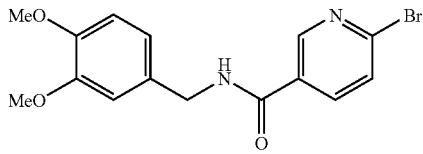 [SMILES: COc1ccc(CNC(=O)c2ccc(Br)nc2)cc1OC]

To a mixture consisting of 6-bromonicotinic acid (Sigma-Aldrich, 1.5 g), N,N-dicyclohexylcarbodiimide (1.60 g), and dichloromethane (10 mL) was added a solution consisting of veratrylamine (1.24 g) in dichloromethane (10 mL) followed by addition of 1-hydroxybenzotriazole (100 mg). The reaction mixture was stirred overnight at room temperature. The crude reaction mixture was diluted with added dichloromethane (200 mL) and the diluted mixture was washed twice with water (2×100 mL) and once with brine solution (100 mL). The organic phase was subsequently dried over anhydrous sodium sulfate, filtered, and concentrated under reduced pressure to provide a white solid. The product was triturated in ethyl acetate and collected by filtration to afford the title intermediate as a white solid (2.22 g, 85% yield); $R_f$ 0.35 with 3:2 v/v hexanes-ethyl acetate; MS (ESI$^-$) m/z 349, 351.

Step 2: Preparation of N-(3,4-dimethoxybenzyl)-6-phenylnicotinamide (Compound 12)

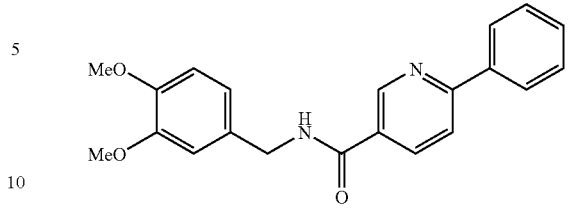

To a mixture consisting of 6-bromo-N-(3,4-dimethoxybenzyl)nicotinamide (1.11 g), phenylboronic acid (0.77 g), and tetrakis(triphenylphosphine)palladium(0) (0.365 g) in N,N-dimethylformamide (20 mL) under a nitrogen atmosphere was added a 2 M aqueous cesium carbonate (6 mL). The stirring mixture was heated to 90° C. for two hours and was subsequently partitioned between ethyl acetate (200 mL) and water (200 mL). The phases were separated and the organic phase was washed twice with fresh portions of water (2×200 mL) and brine solution (150 mL), was dried over anhydrous sodium sulfate, filtered, and concentrated under reduced pressure to provide an orange solid. The solid was triturated with 1:1 v/v hexanes-ethyl acetate and collected by filtration to afford the title compound as a solid (0.447 g, 40.6% yield); $^1$H-NMR (300 MHz; CDCl$_3$) δ 9.06 (d, 1H, J=2.1 Hz), 8.20 (dd, 1H, J=8.4, 2.4 Hz), 8.05-8.01 (m, 2H), 7.81 (dd, 1H, J=8.4, 0.6 Hz), 7.51-7.47 (m, 3H), 6.92-6.84 (m, 3H), 6.51 (broad t, 1H), 4.62 (d, 2H, J=5.7 Hz), 3.891 (s, 3H), 3.888 (s, 3H); $R_f$ 0.17 with 7:3 v/v hexanes-ethyl acetate; MS (APCI$^+$) m/z 349 (M+1).

Example 5

Preparation of (2-phenylpyrimidin-5-yl)(piperazin-1-yl)methanone (Compound 13)

Step 1: Preparation of tert-butyl 4-(2-phenylpyrimidine-5-carbonyl)piperazine-1-carboxylate

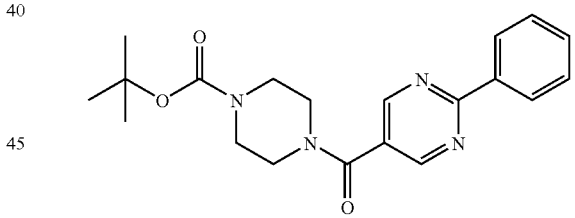

To a mixture consisting of tert-butyl piperazine-1-carboxylate (465 mg), 2-phenylpyrimidine-5-carboxylic acid (Compound 17; synthesis described in Example 1, Steps 1-3 of WO 2007/041634; 450 mg), 1-hydroxybenzotriazole (304 mg), and N-methyl-morpholine (0.275 mL) in N,N-dimethylformamide (32 mL) was added 1-(dimethylaminopropyl)-3-ethylcarbodiimide hydrochloride (EDAC, 646 mg) and the mixture was stirred for thirty minutes. The mixture was diluted with ethyl acetate (250 mL) and washed four times with water (4×300 mL) and once with brine solution. The organic phase was dried, filtered, and concentrated under reduced pressure to afford the title intermediate as a white solid (587 mg, 71% yield); MS (ESI$^+$) m/z 369 (M+1); HPLC (Column: 2.1×150 mm, 3μ GeminiC18; detection wavelength: 210 nm; mobile phase A: 90/10H$_2$O/CH$_3$CN 10 mM NH$_4$OAc; mobile phase B: 10/90H$_2$O/CH$_3$CN 10 mM NH$_4$OAc; gradient: 0-6 minutes 0-100% B, 6-10 minutes 100% B, 10.1-15 minutes 0% B; flow rate: 0.25 mL/min) purity: 97.2%, retention time: 11.9 minutes.

Step 2: Preparation of (2-phenylpyrimidin-5-yl)(piperazin-1-yl)methanone (Compound 13)

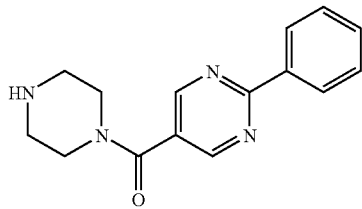 [SMILES: O=C(c1cnc(-c2ccccc2)nc1)N1CCNCC1]

To a mixture consisting of tert-butyl 4-(2-phenylpyrimidine-5-carbonyl)piperazine-1-carboxylate (587 mg) in dichloromethane (8 mL) at 0° C. was added trifluoroacetic acid (7 mL). The mixture was stirred cold for one hour and was subsequently concentrated under reduced pressure to provide a residue, which was purified by flash silica column chromatography. Elution with 95:5 dichloromethane-methanol with 0.5% concentrated ammonium hydroxide afforded the title compound (400 mg, 94% yield); MS (ESI$^+$) m/z 269 (M+1); HPLC (Column: 2.1×150 mm, 3μGeminiC18; detection wavelength: 210 nm; mobile phase A: 90/10H$_2$O/CH$_3$CN 10 mM NH$_4$OAc; mobile phase B: 10/90H$_2$O/CH$_3$CN 10 mM NH$_4$OAc; gradient: 0-6 minutes 0-100% B, 6-10 minutes 100% B, 10.1-15 minutes 0% B; flow rate: 0.25 mL/min) purity: 98.5%, retention time: 9.7 minutes.

Example 6

Preparation of detection analyte 2-(6-hydroxy-3-oxo-3H-xanthen-9-yl)-5-(2-(3-((2-phenylpyrimidine-5-carboxamido)methyl)phenylsulfonamido)ethylcarbamoyl)benzoic acid (Compound 20)

Step 1: Preparation of tert-butyl 2-(3-cyanophenylsulfonamido)-ethylcarbamate (Compound 15)

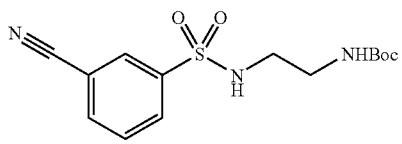 [SMILES: CC(C)(C)OC(=O)NCCNS(=O)(=O)c1cccc(C#N)c1]

To a stirring mixture consisting of tert-butyl 2-aminoethylcarbamate (Sigma-Aldrich, 832 mg), triethylamine (1.44 mL), and 1,4-dioxane (25 mL) was added 3-cyanobenzene-1-sulfonyl chloride (Compound 14, Sigma-Aldrich, 942 mg) and the mixture was stirred overnight. The solvent was removed under reduced pressure and the residue was partitioned between ethyl acetate and 5% aqueous potassium hydrogen sulfate. The organic phase was washed with brine, dried over magnesium sulfate, filtered, and concentrated under reduced pressure to afford the title intermediate (1.52 g), which was carried on without further purification.

Step 2: Preparation of tert-butyl 2-(3-(aminomethyl)phenylsulfonamido)-ethylcarbamate (Compound 16)

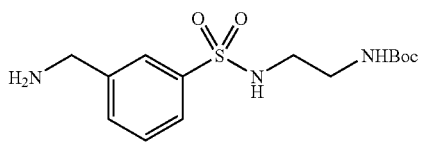 [SMILES: CC(C)(C)OC(=O)NCCNS(=O)(=O)c1cccc(CN)c1]

To a mixture consisting of crude tert-butyl 2-(3-cyanophenylsulfonamido)-ethylcarbamate (Compound 15, 1.52 g) in methanol (46 mL) under a nitrogen atmosphere was added 5% palladium on carbon (1 g). Hydrogen gas was applied via balloon at atmospheric pressure. The reaction mixture was stirred vigorously for two hours and was subsequently filtered over Celite and rinsed with additional methanol. The mixture was concentrated under reduced pressure and purified by silica chromatography (5:95 methanol-dichloromethane) to afford the title intermediate (650 mg, 42% over two steps).

Step 3: Preparation of tert-butyl 2-(3-((2-phenylpyrimidine-5-carboxamido)methyl)phenylsulfonamido)ethylcarbamate (Compound 18)

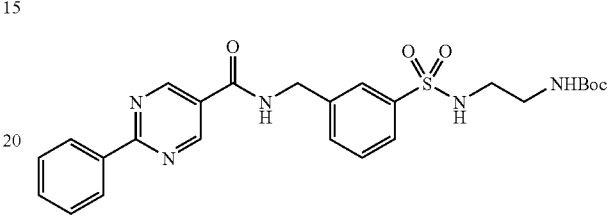

To a mixture consisting of tert-butyl 2-(3-(aminomethyl)phenylsulfonamido)ethylcarbamate (Compound 16, 278 mg), 2-phenylpyrimidine-5-carboxylic acid (Compound 17; synthesis described in Example 1, Steps 1-3 of WO 2007/041634 to Aldous et al., entitled "Pyrimidine Amide Compounds as PGDS Inhibitors"; 182 mg), HOBt (123 mg), and N-methyl-morpholine (0.11 mL) in N,N-dimethylformamide (11 mL) was added 1-(dimethylaminopropyl)-3-ethylcarbodiimide hydrochloride (287 mg) and the mixture was stirred for 2.5 hours. The crude reaction mixture was diluted with ethyl acetate and washed with brine. The organic phase was dried (MgSO$_4$), filtered and concentrated under reduced pressure. The residue was purified by silica chromatography (5:95 methanol-dichloromethane) to afford the title intermediate (363 mg, 87%); MS (ESI$^-$) m/z 510 (M−1).

Step 4: Preparation of N-(3-(N-(2-aminoethyl)sulfamoyl)benzyl)-2-phenylpyrimidine-5-carboxamide (Compound 19)

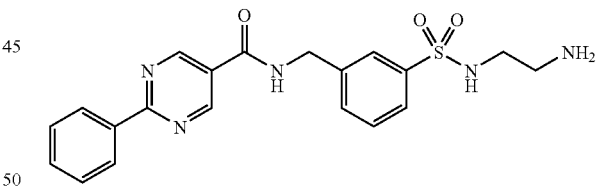

To a stirring mixture consisting of tert-butyl 2-(3-((2-phenylpyrimidine-5-carboxamido)methyl)phenylsulfonamido)ethylcarbamate (Compound 18, 336 mg) in dichloromethane (4 mL) at 0° C. was added trifluoroacetic acid (4 mL) and the mixture was stirred for 1.5 hours. The reaction mixture was quenched with saturated aqueous sodium bicarbonate, extracted into ethyl acetate thrice and washed with brine. The organic phase was dried (MgSO$_4$), filtered and concentrated under reduced pressure. The residue was purified by silica chromatography (5:95 methanol-dichloromethane) to afford the title intermediate (270 mg, 90%); melting point 135-137° C.; $^1$H NMR (400 MHz, DMSO-d$_6$) δ 2.51 (t, 2 H), 2.72 (t, 2 H), 3.0-4.0 (bs, 3 H), 4.61 (d, 2 H), 7.54-7.64 (m, 5 H), 7.68 (d, 1 H), 7.75 (s, 1 H), 8.44 (dd, 2 H), 9.29 (s, 2 H), 9.52 (t, 1 H); MS (ESI$^+$) m/z 413 (M+1); H-PGDS-MBP FP assay IC$_{50}$ (with Compound 20 as the detection analyte): 200-300 nM.

Step 5: Preparation of 2-(6-hydroxy-3-oxo-3H-xanthen-9-yl)-5-(2-(3-((2-phenylpyrimidine-5-carboxamido)methyl)phenylsulfonamido)ethylcarbamoyl)benzoic acid (Compound 20)

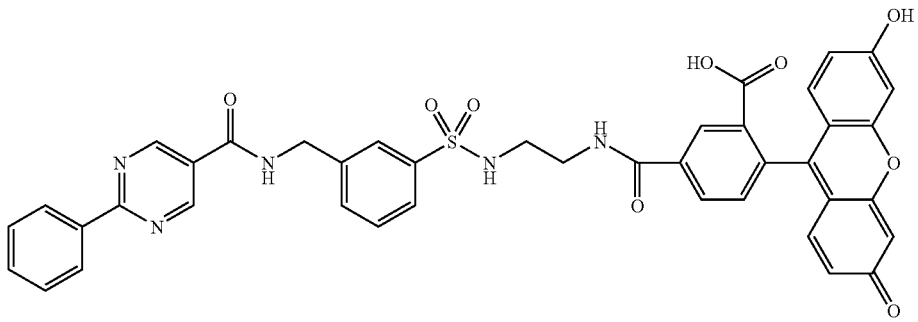 [SMILES: O=C(NCCNS(=O)(=O)c1cccc(CNC(=O)c2cnc(-c3ccccc3)nc2)c1)c1ccc(-c2c3ccc(=O)cc-3oc3cc(O)ccc23)c(C(=O)O)c1]

To a mixture consisting of N-(3-(N-(2-aminoethyl)sulfamoyl)benzyl)-2-phenylpyrimidine-5-carboxamide (Compound 19, 8.7 mg) in N,N-dimethylformamide (1 mL) was added 250 mM potassium phosphate buffer, pH 8 (2 mL) and 5-carboxyfluorescein, succinimidyl ester (5-FAM, SE; Biotium Catalog No. 90029; 10 mg). The mixture was stirred in the dark until the reaction was complete. The crude product was purified by preparative thin-layer chromatography (75:15:2 chloroform-methanol-water) to afford the title compound (approximately 4 mg); MS (ESI$^-$) m/z 768 (M−1).

Example 7

Preparation of detection analyte N-(3-(N-(2-(5-carbonyl-X-rhodamine)amino)ethyl)sulfamoyl)benzyl)-2-phenylpyrimidine-5-carboxamide (Compound 21)

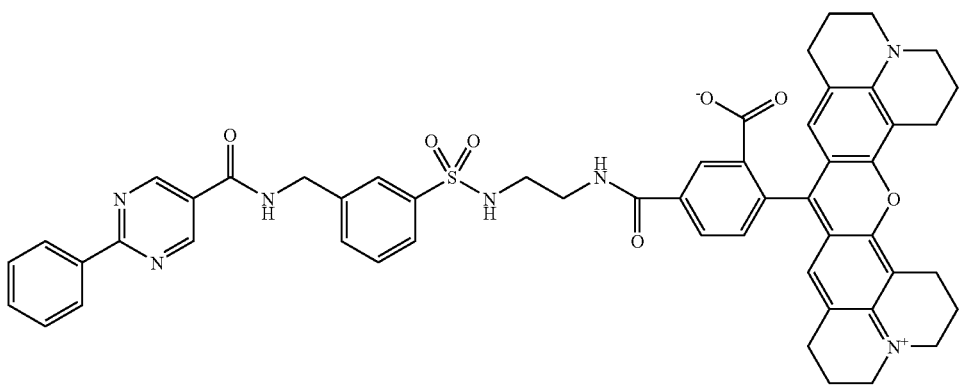

To a mixture consisting of N-(3-(N-(2-aminoethyl)sulfamoyl)benzyl)-2-phenylpyrimidine-5-carboxamide (Compound 19 from Example 6, Step 4 above, 5 mg) in N,N-dimethylformamide (1 mL) was added 250 mM potassium phosphate buffer, pH 8 (2 mL) and 5-carboxy-X-rhodamine, succinimidyl ester (5-ROX, SE; Biotium Catalog No. 90036 (NEED YEAR); 5 mg) in N,N-dimethylformamide (1 mL) followed by a N,N-dimethylformamide rinse (0.5 mL). The mixture was stirred overnight in the dark. The crude product was purified by preparative thin-layer chromatography (75:15:2 chloroform-methanol-water) to afford the title compound (approximately 2 mg); MS (ESI$^-$) m/z 927 (M−1).

Example 8

Preparation of detection analyte N-(3-(N-(2-(DyLight™ 633)amino)ethyl)sulfamoyl)benzyl)-2-phenylpyrimidine-5-carboxamide (Compound 22)

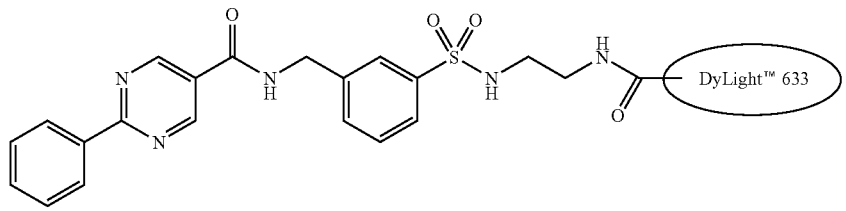 [SMILES: CC(=O)NCCNS(=O)(=O)c1cccc(CNC(=O)c2cnc(-c3ccccc3)nc2)c1]

To a mixture consisting of N-(3-(N-(2-aminoethyl)sulfamoyl)benzyl)-2-phenylpyrimidine-5-carboxamide (Compound 19 from Example 6, Step 4 above, 1 mg) in N,N-dimethylformamide (100 µL) was added 0.05 M sodium borate buffer, pH 8.5 (400 µL) and DyLight™ 633 NHS ester (Thermo Scientific/Pierce Biotechnology Catalog No. 46414; 1 mg) in N,N-dimethylformamide (200 µL) followed by a N,N-dimethylformamide rinse (200 µL). The mixture was stirred overnight in the dark. The crude product was purified by reverse-phase preparative thin-layer chromatography (solvent system 1:1 v/v ethanol-water) to afford the title compound; MS (ESI$^+$) m/z 1341, 1363 (M+1), 1385 (M+Na$^+$); UV-VIS ($\lambda_{max}$, nm) 205, 275, 620; HPLC (Column: Agilent Technologies 2.1×50 mm, 3.5 µm Zorbax SB-C18, part number 871700-902, serial #USFC0020077; mobile phase A: 90:10:0.1H$_2$O/MeOH/AcOH; mobile phase B: 90:10:0.1 MeOH/H$_2$O/AcOH; gradient: 0-6 minutes 0-100% B, 6-9 minutes 100% B, 9.1-15 minutes 0% B; flow rate: 0.4 mL/min; temperature: 35° C.) purity: 100%, retention time: 5.51 minutes.

Example 9

Cloning, Expression, Purification, and Characterization of H-PGDS-MBP Fusion Protein MBP-H-PGDS Protocol (a). Cloning Amino acids 2-199 of the following sequence were inserted in the BamHI and HindIII sites of a pMAL-c2X vector: (accession number NM_014485 shown in bold):

This yielded an N-terminal maltose binding protein tagged human hematopoietic PGDS, as shown in FIG. 6. The clone was then transformed into the expression strain BL21 (DE3) star cells and a glycerol stock was generated. The expected size is 66.29 kDa.

(b). Expression

This protein was grown from the above glycerol stock in LB containing 100 mg/L ampicillin at 37° C. until an OD of 0.4-0.6 was obtained. The culture was then induced with isopropyl-β-D-1-thiogalactopyranoside (IPTG) to a final concentration of 1 mM. The cultures were harvested ~18 hours post induction and the cell pellets were stored at −80° C.

(c). Purification

The cell pellets were resuspended in 20 mM Tris-HCl pH 7.4 containing 200 mM NaCl, 1 mM EDTA, 0.1 mg/ml lysozyme, and protease inhibitor cocktail then sonicated for cell lysis. The lysed cell suspension was then centrifuged at ~30,000×g for 30 minutes. The supernatant was bound to amylose resin overnight at 4° C. with rocking. The resin binding buffer was 20 mM Tris-HCl pH 7.4 containing 200 mM NaCl and 1 mM EDTA. The resin was then washed 3 times with the binding buffer and the purified MBP-H-PGDS was eluted using 20 mM Tris-HCl pH 7.4 containing 200 mM NaCl, 1 mM EDTA and 10 mM maltose.

(d). Characterization

Protein concentration was determined on the purified sample using BCA, Bradford, and A280 determination methods. Coomassie electrophoresis was performed to examine purity of the protein. Specific activity was determined using the kinetic formation of PGD$_2$ from PGH$_2$ then quantitated using Cayman's PGD$_2$ EIA Kit.

(e). Assay Conditions (125 µl Total Volume Performed at Room Temperature)

1. Buffer: 100 mM Tris-HCl pH 8.0
2. 1 mM Glutathione-reduced
3. 40 µM PGH$_2$
4. 1 mM MgCl$_2$
5. 940 ng MBP-H-PGDS Initiated reaction with PGH$_2$ and took time points at 0, 15, 30, and 45 seconds. Each time point was quenched in 20 mM FeCl$_2$ to prevent any additional reaction from occurring by driving any unconverted PGH$_2$ into 12-HHT. The quenched samples were diluted 1:5000 in EIA buffer (100 mM phosphate, pH 7.4 containing 0.01% NaN$_3$, 0.4M NaCl, 1 mM EDTA, and 0.1% BSA) for use in the PGD$_2$ EIA Kit.

What is claimed is:

1. A detection analyte comprising: 2-(6-hydroxy-3-oxo-3H-xanthen-9-yl)-5-(2-(3-((2-phenylpyrimidin-e-5-carboxamido)methyl) phenylsulfonamido) ethylcarbamoyl) benzoic acid.

* * * * *

UNITED STATES PATENT AND TRADEMARK OFFICE
CERTIFICATE OF CORRECTION

PATENT NO. : 8,440,417 B2
APPLICATION NO. : 12/465332
DATED : May 14, 2013
INVENTOR(S) : Kirk M. Maxey et al.

It is certified that error appears in the above-identified patent and that said Letters Patent is hereby corrected as shown below:

Title Page, Item (75) Inventors: delete "Kirk W. Maxey" add --Kirk M. Maxey--

Signed and Sealed this
Eighth Day of October, 2013

Teresa Stanek Rea
*Deputy Director of the United States Patent and Trademark Office*

SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence

```
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 591
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
290                 295                 300

Leu Lys Ser Tyr Glu Glu Glu Leu Ala Lys Asp Pro Arg Ile Ala Ala
305                 310                 315                 320
```

-continued

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Pro Asn Tyr Lys Leu Thr Tyr
385                 390                 395                 400

Phe Asn Met Arg Gly Arg Ala Glu Ile Ile Arg Tyr Ile Phe Ala Tyr
                405                 410                 415

Leu Asp Ile Gln Tyr Glu Asp His Arg Ile Glu Gln Ala Asp Trp Pro
            420                 425                 430

Glu Ile Lys Ser Thr Leu Pro Phe Gly Lys Ile Pro Ile Leu Glu Val
        435                 440                 445

Asp Gly Leu Thr Leu His Gln Ser Leu Ala Ile Ala Arg Tyr Leu Thr
    450                 455                 460

Lys Asn Thr Asp Leu Ala Gly Asn Thr Glu Met Glu Gln Cys His Val
465                 470                 475                 480

Asp Ala Ile Val Asp Thr Leu Asp Asp Phe Met Ser Cys Phe Pro Trp
                485                 490                 495

Ala Glu Lys Lys Gln Asp Val Lys Glu Gln Met Phe Asn Glu Leu Leu
            500                 505                 510

Thr Tyr Asn Ala Pro His Leu Met Gln Asp Leu Asp Thr Tyr Leu Gly
        515                 520                 525

Gly Arg Glu Trp Leu Ile Gly Asn Ser Val Thr Trp Ala Asp Phe Tyr
    530                 535                 540

Trp Glu Ile Cys Ser Thr Thr Leu Leu Val Phe Lys Pro Asp Leu Leu
545                 550                 555                 560

Asp Asn His Pro Arg Leu Val Thr Leu Arg Lys Val Gln Ala Ile
                565                 570                 575

Pro Ala Val Ala Asn Trp Ile Lys Arg Arg Pro Gln Thr Lys Leu
            580                 585                 590

<210> SEQ ID NO 3
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met His His His His His Pro Asn Tyr Lys Leu Thr Tyr Phe Asn
1               5                   10                  15

Met Arg Gly Arg Ala Glu Ile Ile Arg Tyr Ile Phe Ala Tyr Leu Asp
            20                  25                  30

Ile Gln Tyr Glu Asp His Arg Ile Glu Gln Ala Asp Trp Pro Glu Ile
        35                  40                  45

Lys Ser Thr Leu Pro Phe Gly Lys Ile Pro Ile Leu Glu Val Asp Gly
    50                  55                  60

Leu Thr Leu His Gln Ser Leu Ala Ile Ala Arg Tyr Leu Thr Lys Asn
65                  70                  75                  80

Thr Asp Leu Ala Gly Asn Thr Glu Met Glu Gln Cys His Val Asp Ala
                85                  90                  95

-continued

| | | | | | | | | | | | | |
|---|---|---|---|---|---|---|---|---|---|---|---|---|
|Ile|Val|Asp|Thr|Leu|Asp|Asp|Phe|Met|Ser|Cys|Phe|Pro|Trp|Ala|Glu|
| | | |100| | | |105| | | |110| | | | |
|Lys|Lys|Gln|Asp|Val|Lys|Glu|Gln|Met|Phe|Asn|Glu|Leu|Leu|Thr|Tyr|
| | |115| | | |120| | | |125| | | | | |
|Asn|Ala|Pro|His|Leu|Met|Gln|Asp|Leu|Asp|Thr|Tyr|Leu|Gly|Gly|Arg|
| |130| | | |135| | | |140| | | | | | |
|Glu|Trp|Leu|Ile|Gly|Asn|Ser|Val|Thr|Trp|Ala|Asp|Phe|Tyr|Trp|Glu|
|145| | | |150| | | |155| | | |160| | | |
|Ile|Cys|Ser|Thr|Thr|Leu|Leu|Val|Phe|Lys|Pro|Asp|Leu|Leu|Asp|Asn|
| | | |165| | | |170| | | |175| | | | |
|His|Pro|Arg|Leu|Val|Thr|Leu|Arg|Lys|Lys|Val|Gln|Ala|Ile|Pro|Ala|
| | |180| | | |185| | | |190| | | | | |
|Val|Ala|Asn|Trp|Ile|Lys|Arg|Arg|Pro|Gln|Thr|Lys|Leu|
| |195| | | |200| | | |205| | | | | | |